United States Patent
Sacks et al.

(10) Patent No.: US 6,702,989 B2
(45) Date of Patent: Mar. 9, 2004

(54) PULSED CARRIER GAS FLOW MODULATION FOR SELECTIVITY ENHANCEMENTS WITH GAS CHROMATOGRAPHY USING SERIES-COUPLED COLUMN ENSEMBLES

(75) Inventors: Richard Douglas Sacks, Ann Arbor, MI (US); Joshua Jonathan Mark Whiting, Whitmore Lake, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/154,409

(22) Filed: May 23, 2002

(65) Prior Publication Data

US 2003/0108448 A1 Jun. 12, 2003

Related U.S. Application Data

(63) Continuation-in-part of application No. 10/055,022, filed on Jan. 22, 2002, which is a continuation-in-part of application No. 10/016,798, filed on Dec. 10, 2001.

(51) Int. Cl.[7] .............................................. G01N 30/32
(52) U.S. Cl. ..................... 422/89; 73/23.36; 73/23.42; 95/86; 96/102; 96/103; 96/104; 436/161
(58) Field of Search ........................... 422/89; 436/161; 73/23.35, 23.36, 23.37, 23.42; 95/82, 86; 96/101, 102, 103, 104, 106

(56) References Cited

U.S. PATENT DOCUMENTS

| | | |
|---|---|---|
| 4,925,306 A | 5/1990 | Sacks et al. |
| 5,096,471 A | 3/1992 | Sacks et al. |
| 5,141,532 A | 8/1992 | Sacks et al. |
| 5,141,534 A | 8/1992 | Sacks et al. |
| 5,205,845 A | 4/1993 | Sacks et al. |
| 5,281,256 A | 1/1994 | Sacks et al. |
| 5,288,310 A | 2/1994 | Peters et al. |

OTHER PUBLICATIONS

Instrumental Methods of Analysis, Sixth Edition, Willard et al, eds., Wadsworth Publishing Company, Belmont, Ca (1981) pp. 465 and 570.*

Leonard et al., Anal. Chem. (1999), vol. 71, pp. 5501–5507.*

Tincuta Veriotti, Megan McGuigan, and Richard Sacks, "Pulsed Flow Modulation for High–Speed GC Using a Pressure–Tunable Column Emsemble", Analytical Chemistry 2001, vol. 73, No. 2, Jan. 15, 2001, pp. 279–285, Published on Web Dec. 14, 2000.

(List continued on next page.)

Primary Examiner—Jan Ludlow
(74) Attorney, Agent, or Firm—Harness, Dickey & Pierce, P.L.C.

(57) ABSTRACT

A gas chromatography system having a computer-controlled venting valve system that delivers pressurized pulses to a column junction point of two series-coupled columns having different stationary-phase chemistries and a method of using the same. Each pressurized pulse causes a differential change in the carrier gas velocities in the two columns, which lasts for the duration of the pressurized pulse. Whereby, the pressurized pulse selectively increases the separation of a component pair that exhibits separation at the exit of the first column, but otherwise co-elutes from the column ensemble.

8 Claims, 16 Drawing Sheets

OTHER PUBLICATIONS

Tincuta Veriotti and Richard Sacks, "A Tandem Column Ensemble with an Atmospheric Pressure Junction–Point Vent for High–Speed GC with Selective Control of Peak–Pair Separation", Analytical Chemistry 2001, vol. 73, No. 4, Feb. 15, 2001, pp. 813–919, Published on Web Jan. 23, 2001.

Tincuta Veriotti and Richard Sacks, "High–Speed GC and GC/MS with a Series–Coupled Column Ensemble Using Stop–Flow Operation", Analytical Chemistry 2001, vol. 73, No. 13, Jul. 1, 2001, pp. 3045–3050, Published on Web May 17, 2001, Tincuta Veriotti and Richard Sacks, "High–Speed GC and GC/Time–of–Flight MS of Lemon and Lime Oil Samples", Analytical Chemistry 2001, vol. 73, No. 18, Sep. 15, 2001, pp. 4395–4402, Published on Web Aug. 10, 2001.

Joshua Whiting and Richard Sacks, "Selectivity Enhancement for High–Speed GC Analysis of Volatile Organic Compounds with Portable Instruments Designed for Vacuum–Outlet and Atmospheric–Pressure Inlet Operation Using Air as the Carrier Gas", Analytical Chemistry 2002, vol. 74, No. 1, Jan. 1, 2002, pp. 246–252, Published on Web Nov. 28, 2001.

* cited by examiner

PULSED CARRIER GAS FLOW MODULATION FOR SELECTIVITY ENHANCEMENTS WITH GAS CHROMATOGRAPHY USING SERIES-COUPLED COLUMN ENSEMBLES

CROSS-REFERENCE TO RELATED APPLICATIONS

This application is a continuation-in-part of U.S. Pat. application Ser. No. 10/055,022 filed on Jan. 22, 2002, which is a continuation-in-part of U.S. patent application Ser. No. 10/016,798 filed on Dec. 10, 2001. The disclosures of the above applications are incorporated herein by reference.

FIELD OF THE INVENTION

The present invention relates to chemical mixture analysis and, more particularly, relates to a practical approach for achieving improved selectivity for capillary gas chromatography.

BACKGROUND OF THE INVENTION

Gas chromatography is an analytical technique for separating compounds from a mixture based on their volatilities and polarities. Gas chromatography thus provides both qualitative and quantitative information for the individual compounds present in a sample. These compounds move through a gas chromatography column as gases, either because the compounds are normally gases or because they have been heated and vaporized into a gaseous state. The compounds partition between a stationary phase, which can be either solid or liquid, and a mobile phase, which is typically gas.

As is known in the art, the introduction of the fused silica, wall-coated, capillary gas chromatography column in 1979 represented a paradigm shift in the analysis of volatile and semi-volatile organic compounds. However, with the introduction of the fused-silica capillary column, the emphasis gradually shifted towards the development of more universal columns with greater resolving power for a wider variety of compound mixtures.

Long capillary columns (generally greater than 20 m long) generally provide greater resolving power and, thus, the complete separation of more complex mixtures with analysis times comparable to those achieved with packed columns.

Briefly, as used herein, "selectivity" generally refers to the pattern of peaks produced from the gas chromatography column and the values of the retention factor ratios for all component pairs. Retention factor is equal to the difference between the retention time and the column void time ratioed to the void time. The greater the selectivity of the column for a specified component pair, the more separation between the corresponding peaks of the chromatogram can be achieved.

On the other hand, shorter capillary columns (generally 5–20 m long), which are operated at relatively high carrier gas flow rates, have been used to obtain faster mixture separations. However, in exchange for faster mixture separations, resolving power is sacrificed. As should be appreciated, if these techniques for high-speed gas chromatography are to be useful for more complex mixtures, selectivity or resolving power must be improved.

Accordingly, there exists a need in the relevant art to provide a method and apparatus whereby a wide variety of compounds may be quickly separated without significant losses in resolution. Furthermore, there exists a need in the relevant art to provide a method and apparatus of capillary column gas chromatography that is capable of varying the selectivity during the course of the compound analysis to provide improved selectivity capability for various specific compound pairs. Still further, there exists a need in the relevant art to provide a method and apparatus of pulsed carrier gas flow modulation for improved selectivity of gas chromatography. Additionally, there exists a need in the relevant art to provide a method of capillary gas chromatography that overcomes the disadvantages of the prior art.

SUMMARY OF THE INVENTION

According to the principles of the present invention, a gas chromatography system is provided having an advantageous construction and method of using the same. The gas chromatography system includes a computer-controlled venting valve system that delivers pressurized pulses to a column junction point of two series-coupled columns having different stationary-phase chemistries. Each pressurized pulse causes a differential change in the carrier gas velocities in the two columns, which lasts for the duration of the pressurized pulse. Whereby, the pressurized pulse selectively increases the separation of a component pair that exhibits separation at the exit of the first column, but otherwise co-elutes from the column ensemble.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2(*b*) is a graph illustrating application of a pressurized pulse to the pair of illustrative components after one of the components has reached the column junction point;

FIG. 2(*c*) is a graph illustrating application of a pressurized pulse to the pair of illustrative components after both components have reached the column junction point;

FIG. 2(*d*) is an enlarged graph and chromatogram of box 1(*d*) of FIG. 2(*a*);

FIG. 2(*e*) is an enlarged graph and chromatogram of box 1(*e*) of FIG. 2(*b*);

FIG. 2(*f*) is an enlarged graph and chromatogram of box 1(*f*) of FIG. 2(*c*);

DETAILED DESCRIPTION OF THE PREFERRED EMBODIMENTS

The following description of the preferred embodiments is merely exemplary in nature and is in no way intended to limit the invention, its application, or uses.

As will be described in detail herein, the first embodiment of the present invention provides a method and apparatus for achieving improved selectivity for gas chromatography with capillary columns. This embodiment comprises a computer-controlled pressure controller that delivers pressurized pulses to a column junction point of two series-coupled columns having different stationary-phase chemistries. Each pressurized pulse causes a differential change in the carrier gas velocities in the two columns, which lasts for the duration of the pressurized pulse. The pressurized pulse selectively increases the separation of a component pair that exhibits separation at the exit of the first column, but otherwise co-elutes from the column ensemble. If both components are on the same column when the pressurized pulse is applied, the component separation remains essentially unchanged despite an overall shift in retention times. If one component of the pair is on the first column and the other component is on the second column, a pressurized pulse can result in a large change in the ensemble separation for the component pair, thereby increasing the peak separation in the chromatogram to aid in quantitation and identification.

A significant limitation of known prior art methods is the fact that a change in the pressure at the column junction point used to increase the separation of a particular component pair often results in reduced separation of one or more other component pairs. Thus, the selection of a pressure at the column junction point for a specified set of target compounds previously required a compromise. However, the present invention preferably employs a relatively short pressurized pulse to increase the separation of a specific component pair without significantly affecting the peak pattern and separation of the remaining components in the mixture.

Figure 1:
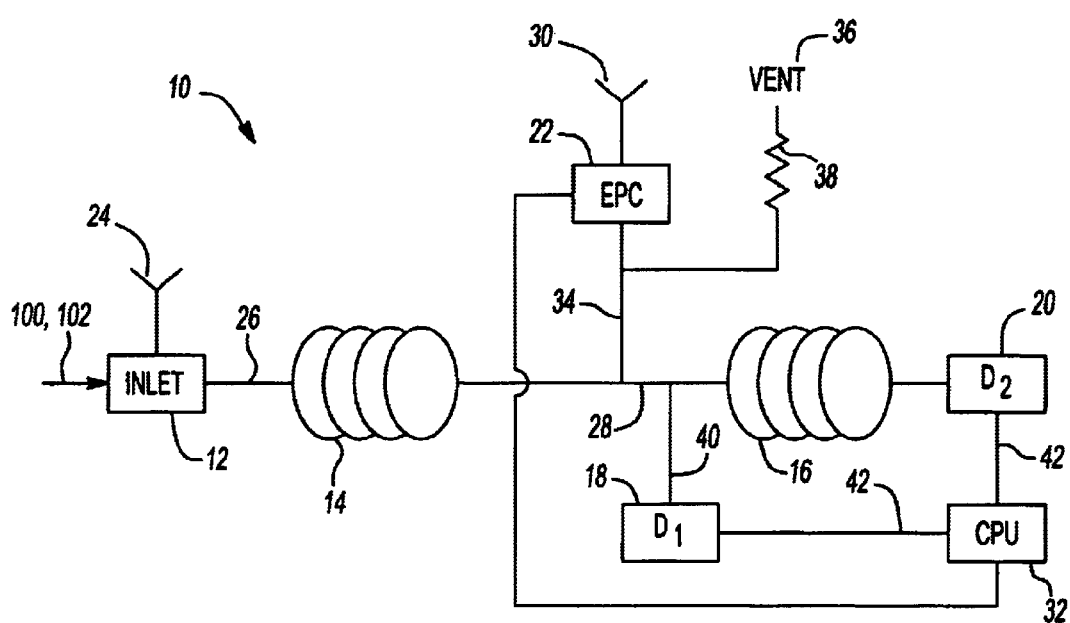
FIG. 1 is a schematic drawing illustrating a gas chromatography system according to a first embodiment of the present invention.

Referring now to FIG. 1, a pressure-controlled, dual-column, gas chromatography system is schematically illustrated in accordance with a first embodiment of the present invention, generally indicated at 10. Gas chromatography system 10 generally includes an inlet system 12, a first gas chromatography separation capillary column 14, a second gas chromatography capillary column 16, a first detector ($D_1$) 18, a second detector ($D_2$) 20, and an electronic pressure controller 22.

Inlet system 12 is configured generally to receive a sample "plug" of an analyte mixture for analysis within gas chromatography system 10. More particularly, a stream of carrier gas from a carrier gas supply 24 entrains such analyte mixture during injection. This entrained analyte mixture and carrier gas composite is introduced into first column 14 through a passage 26. Various configurations of inlet system 12 can be provided, such as mechanical injection valves, cryofocusing systems, and the like.

Similarly, first column 14 and second column 16 may take various forms, including columns having various types of liquid stationary phase materials. In addition, solid stationary phase-type columns using adsorbent materials, such as what is commonly known as porous layer open tubular (PLOT) columns or liquid crystal columns. Columns having polar or non-polar stationary phases may be used. However, for discussion purposes in the present disclosure, it is preferred that first column 14 is an approximately 10 m long, 0.25 mm diameter (id) column having a 0.25-$\mu$m thick bonded, stationary-phase, trifluoropropylmethyl polysiloxane film, while second column 16 is an approximately 10 m long, 0.25 mm diameter (id) column having a 0.25-$\mu$m thick bonded, stationary-phase, dimethyl polysiloxane film.

First column 14 and second column 16 are coupled in series along a column junction point 28. Electronic pressure controller 22, which is capable of pressure step sizes of approximately 0.1 psi and pressure repeatability of ±0.01 psi, is fluidly coupled to column junction point 28. An adjustable pressure source carrier gas supply 30 is provided in fluid connection with electronic pressure controller 22 to apply pressurized pulses to column junction point 28 in accordance with the principles of the present invention. Preferably, electronic pressure controller 22 is driven in response to a central processing unit 32. Moreover, electronic pressure controller 22 is preferably coupled to column junction point 28 via an approximately 1.0 m long, 0.1 mm diameter (id) uncoated, fused-silica tube 34. A restrictor member 38 is used to reduce the pressure equilibration time for downward pressure changes and to prevent contamination of electronic pressure controller 22. Preferably, carrier gas supplies 24 and 30 each consists of purified hydrogen, helium, air, or other gases.

Adjustment of this carrier gas pressure via electronic pressure controller 22 results in a differential change in the carrier gas velocities between first column 14 and second column 16, which will result in output changes in the gas chromatogram. That is, an increase in the pressure at column junction point 28 results in reduced carrier gas velocity on first column 14, yet increased velocity on second column 16. If the void time of first column 14 increases and the void time of second column 16 decreases (due to an increase in the pressure at column junction point 28), the mixture components have increased residence time on first column 14 and decreased residence time on second column 16. Consequently, this arrangement increases the influence of the stationary-phase chemistry of first column 14 and decreases the influence of the stationary-phase chemistry of second column 16. Alternatively, a reduction in the pressure at column junction point 28 has the opposite effect.

First detector 18 is coupled to column junction point 28 to monitor a portion of the effluent from first column 14. Similarly, second detector 20 is coupled to the output of second column 16 to monitor the output from second column 16 and, thus, column ensemble 14, 16. Preferably, a 10 m long, 0.10 mm diameter (id), deactivated, fused-silica tube 40 is used to transport approximately 10% of the effluent from first column 14 to first detector 18. As will be described below, a chromatogram is obtained from first detector 18 to determine the time at which to initiate the pressurized pulse from electronic pressure controller 22 to column junction point 28. Preferably, first and second detectors 18 and 20 are each two flame-ionization detectors. However, it should be appreciated that first detector 18 and second detector 20 may be any detector capable of providing sufficient results, such as but not limited to flame-ionization detectors, photo-ionization detectors, thermal-conductivity detectors, solid-state sensors, mass spectrometers, flame photometric detectors, flame thermionic detectors, electron capture detectors, pulse helium ionization detectors, and the like. First detector 18 and second detector 20 each output a resultant signal to central processing unit 32 via communication lines 42. It should be understood that once the pressurized pulse initiation times are determined for a given mixture, first detector 18 may be eliminated, as the initiation time will remain the same for that mixture.

In order to obtain accurate void time values and retention time values for first column 14, the gas transport time from column junction point 28 to first detector 18 along tube 40 is subtracted from the measured retention times outputted from first detector 18. This gas transport time is computed using standard equations for gas flow in capillary tubes. It is further important to note that the gas transport time varies with the pressure at column junction point 28. Retention factors for first column 14 are computed from these corrected retention time and void time values using central processing unit 32. Void time and retention time values for second column 16 are further obtained by central processing unit 32 by subtracting the corresponding values for first column 14 from the ensemble values obtained from second detector 20.

The retention factor values for individual columns as well as the column dimensions and pressures and the viscosity of the carrier gas at the column operating temperature are used as inputs to a band-trajectory model. This band-trajectory model uses spreadsheet calculations and takes into account the carrier gas flow velocity profile along the column axis, the change in retention for each mixture component as it crosses the junction from the first to second column 16, and programmed changes in the pressure at column junction point 28.

Finally, the pressure at column junction point 28 in the absence of the pressurized pulse, also referred to as the quiescent pressure, is further chosen to be equal to the pressure that would occur at column junction point 28 in the absences of any external connections to column junction point 28, also referred to as the natural pressure. This natural pressure results in an ensemble void time that is near the minimum value achievable with the dual-column ensemble.

Discussion of Results

In some cases, a pair of mixture components can co-elute from a tandem-column ensemble if 1) both components have very similar retention factor values on both columns, or 2) if one of the components has a larger retention factor on one of the columns and the other component has a larger retention factor on the other column. In the former case, adjustment of the pressure at column junction point 28 may not separate the two components. Therefore, it may be necessary to use a longer column ensemble, which should provide improved resolving power or an ensemble with greater selectivity for the specific component pair may provide the only solution. However, in the latter case, a change in the pressure at column junction point 28 often will result in adequate separation of the component pair. However as mentioned above, in conventional methods, a change in the pressure at column junction point 28 may result in the co-elution of other component pairs that are previously separated.

Figure 2:
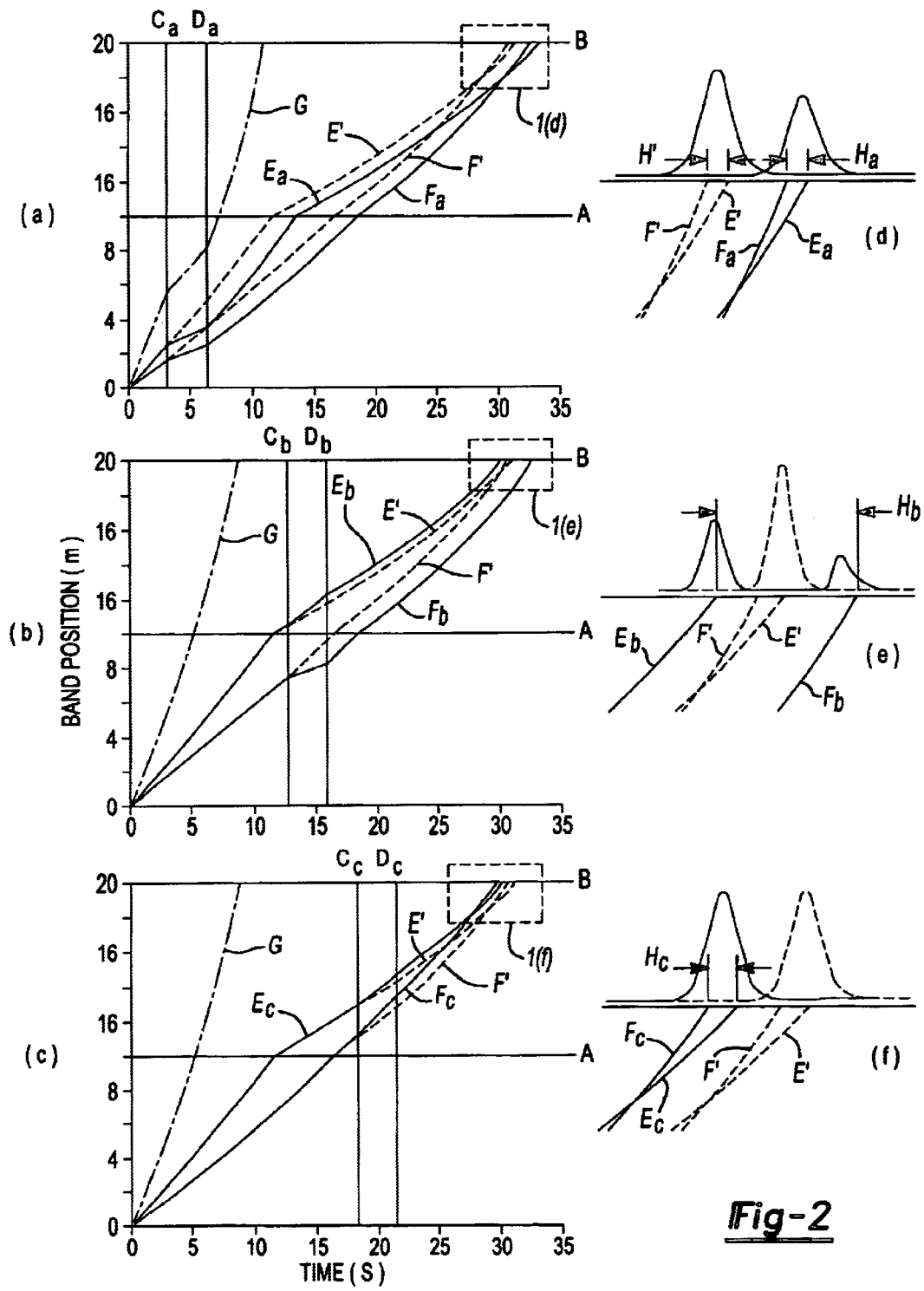
FIG. 2(*a*) is a graph illustrating application of a pressurized pulse to a pair of illustrative components prior to the components reaching a column junction point.

Referring now to FIGS. 2(a)–(c), according to the principles of the present invention the application of a pressurized pulse to column junction point 28 at an appropriate time after injection of the analyte mixture can be used to separate a specific and discrete component pair without significantly affecting the pattern of peaks for other mixture components. In particular, for each of the three cases illustrated in FIGS. 2(a)–(c), injection of the analyte mixture occurs at zero time in the lower left corner of the plots. A horizontal line A in the center of each figure corresponds to column junction point 28. Thus, the area below horizontal line A represent first column 14 and the area above horizontal line A represent second column 16. Therefore, elution from column ensemble 14, 16 occurs along the top horizontal line B at 20 m. A pair of vertical lines, generally indicated at C and D, in each of the three cases illustrates the time interval corresponding to the application of a 3 second wide (nominal) pressurized pulse from a quiescent value of 36.0 psia to 44.0 psia. It should be appreciated that the pressurized pulse may be of any duration necessary to facilitate separation of the component pair. A pair of band trajectories, generally indicated at E and F, represents a first component 100 and a second component 102 of the analyte mixture, respectively (see FIG. 2). For discussion purposes, first component 100 is n-octane and second component 102 is 1-pentanol. In each of FIGS. 2(a)–(c), solid lines, E and F, illustrate the case where a pressurized pulse is used, while the broken line illustrates the case where a pressurized pulse is not used for reference, generally indicated at E' and F'.

Still referring to FIGS. 2(a)–(c), a band trajectory G, represented by a line having alternate dots and dashes, illustrates the trajectory of an unretained component along the column-ensemble axis for the case with the pressurized pulse. As can been seen from FIGS. 2(a)–(c), this line for the unretained component illustrates no discontinuous slope change at column junction point 28. This condition exists because the natural pressure at column junction point 28 is used in the absence of a pulse.

As seen in FIGS. 2(d)–(f), an enlarged portion of FIGS. 2(a)–(c) is illustrated, respectively. More particularly, FIGS. 2(d)–(f) each illustrate the portion of the band trajectory plots in the broken–line box on an expanded time scale and the corresponding chromatograms.

As stated above, first column 14 includes a polar trifluoropropylmethyl polysiloxane stationary phase coating and, thus, first component 100, being the polar 1-pentanol, migrates more slowly therethrough. Similarly, second column 16 includes a non-polar dimethyl polysiloxane coating and, thus, second component 102, being a non-polar n-octane, migrates more slowly therethrough. The result is that in the absence of a pressurized pulse, the band trajectory plots E and F for these components cross just prior to elution from column ensemble 14, 16. The peak apex separation, generally indicated at H', is less than 0.5 seconds, and only a single peak is observed in the chromatogram.

For the case illustrated in FIGS. 2(a) and (d), the pressurized pulse, $C_a$-$D_a$, is applied while both components 100 and 102, illustrated by band trajectories $E_a$ and $F_a$, are still on first column 14 (i.e. below horizontal line A). Since pressurized pulse $C_a$-$D_a$ results in an increase in pressure at column junction point 28, the pressure drop along first column 14 is reduced, and the local migration velocities of both components 100 and 102 are reduced. This effect is illustrated by the shallower slope of band trajectories $E_a$ and $F_a$. This results in greater residence time on first column 14 and the ensemble retention times being shifted to greater values. However, as seen in FIG. 2(d), peak-apex separation $H_a$ is not significantly changed relative to non-pulse peak-apex separation H'.

For the case illustrated in FIGS. 2(b) and (e), the pressurized pulse, $C_b$-$D_b$, is applied after first component 100 has crossed junction point line A, but before second component 102 has reached junction point line A. The larger pressure at column junction point 28 during pressurized pulse $C_b$-$D_b$ results in an increase in local carrier gas velocity on second column 16 (above junction point line A) and, thus, first component 100 accelerates as illustrated by the steeper slope of band trajectory $E_b$. The result is a decrease in ensemble retention time for first component 100. On the other hand, because second component 102 is still on first column 14 (below junction point line A) when pressurized pulse $C_b$-$D_b$ is applied, its migration rate decreases appreciably during pressurized pulse $C_b$-$D_b$. Therefore, band trajectory $F_b$ arrives at junction point line A considerably later than without pressurized pulse $C_a$-$D_a$ (see band trajectory F'). This results in an increase in ensemble retention time. The overall result in this scenario, as seen in FIG. 2(e), is a differential shift in individual retention times for first component 100 and second component 102 as illustrated by peak-apex separation $H_b$.

For the case illustrated in FIGS. 2(c) and (f), the pressurized pulse, $C_c$-$D_c$, is applied after both components 100 and 102 have migrated across junction point line A into second column 16. Since pressurized pulse $C_c$-$D_c$ results in an increase in pressure at column junction point 28, the pressure drop along second column 16 is increased, and the local migration velocities of both components 100 and 102 are sharply increased. This effect is illustrated by the steeper slope of band trajectories $E_c$ and $F_c$. This results in reduced residence time on second column 16 and the ensemble retention times being shifted to smaller values. However, as seen in FIG. 2(f), peak-apex separation $H_c$ is not significantly changed relative to non-pulse peak-apex separation H'.

These results illustrated in FIGS. 2(a)–(f) illustrate that ensemble values of peak-apex separation can be significantly increased for components that are on opposite sides of junction point line A when the pressurized pulse C-D is applied. For components that are on the same side of junction point line A during the pressurized pulse C-D, significant retention time shifts occur, but peak-apex separations and thus the pattern of peaks eluting from column ensemble 14, 16 are not significantly changed.

Figure 5:
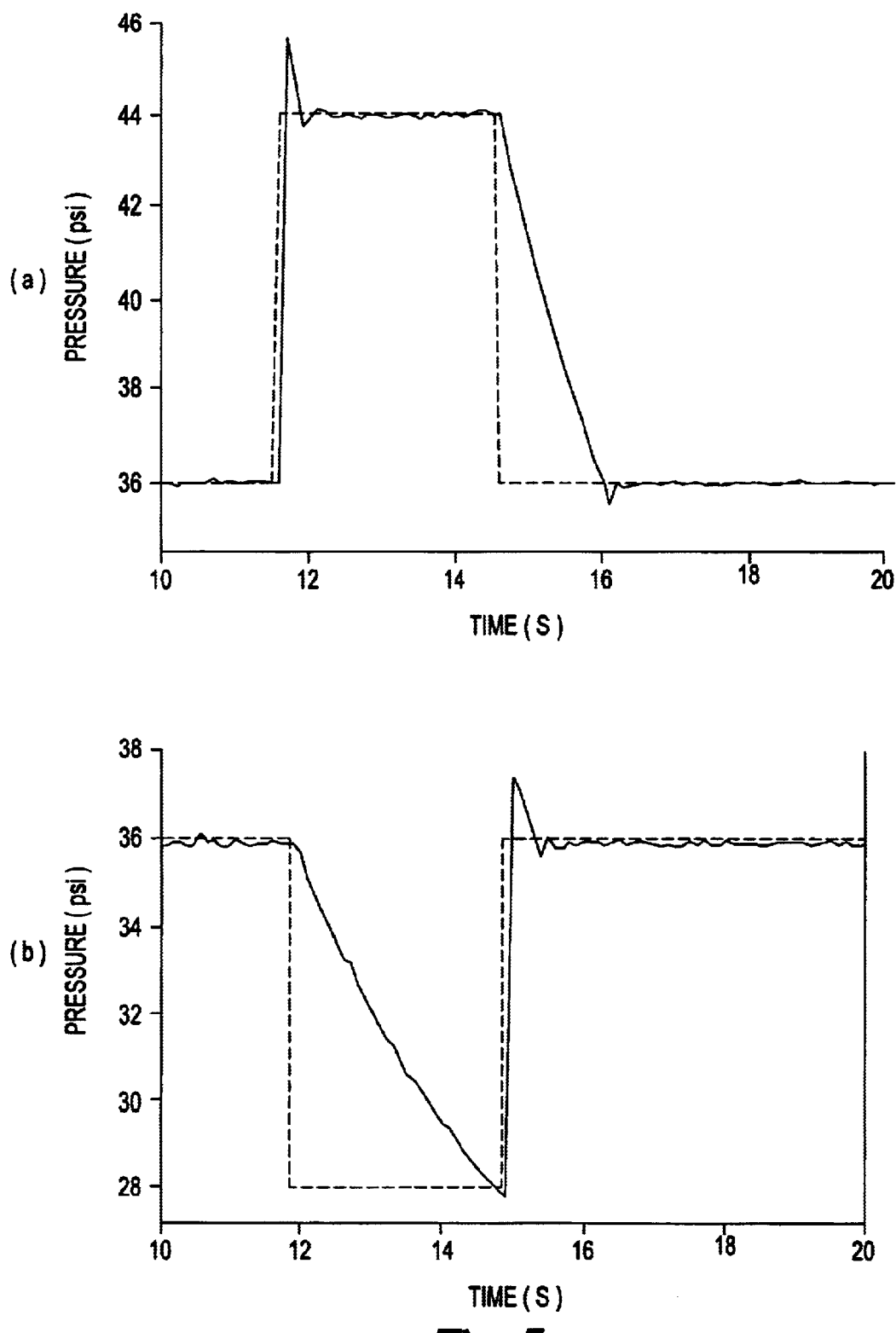
FIG. 5a illustrates an upward pressurized pulse applied to a column junction point, wherein the dashed line illustrates a nominal pulse shape.
FIG. 5b illustrates a downward pressurized pulse applied to the column junction point, wherein the dashed line illustrates a nominal pulse shape.

Referring now to FIGS. 3(a)–(e) and 4(a)–(f), chromatograms obtained with upward and downward pressurized pulses, respectively, initiated at various times after the sample injection are illustrated. Each of the figures is recorded at various pulse-initiation-time-after-injection times. For reference in each of these figures, the peak-apex retention time for a single peak containing both first component 100 and second component 102 is approximately 29.5 seconds, without using a pressurized pulse, as indicated by vertical line Z. As seen in FIGS. 5(a) and (b), the actual pulse shapes are illustrated as an upward pressurized pulse and a downward pressurized pulse, respectively. It may be important to note that an upward pulse (to higher pressure at column junction point 28) results in lower carrier gas velocity on first column 14 and higher velocity on second column 16. The opposite situation occurs for a downward pressurized pulse.

Figure 3:
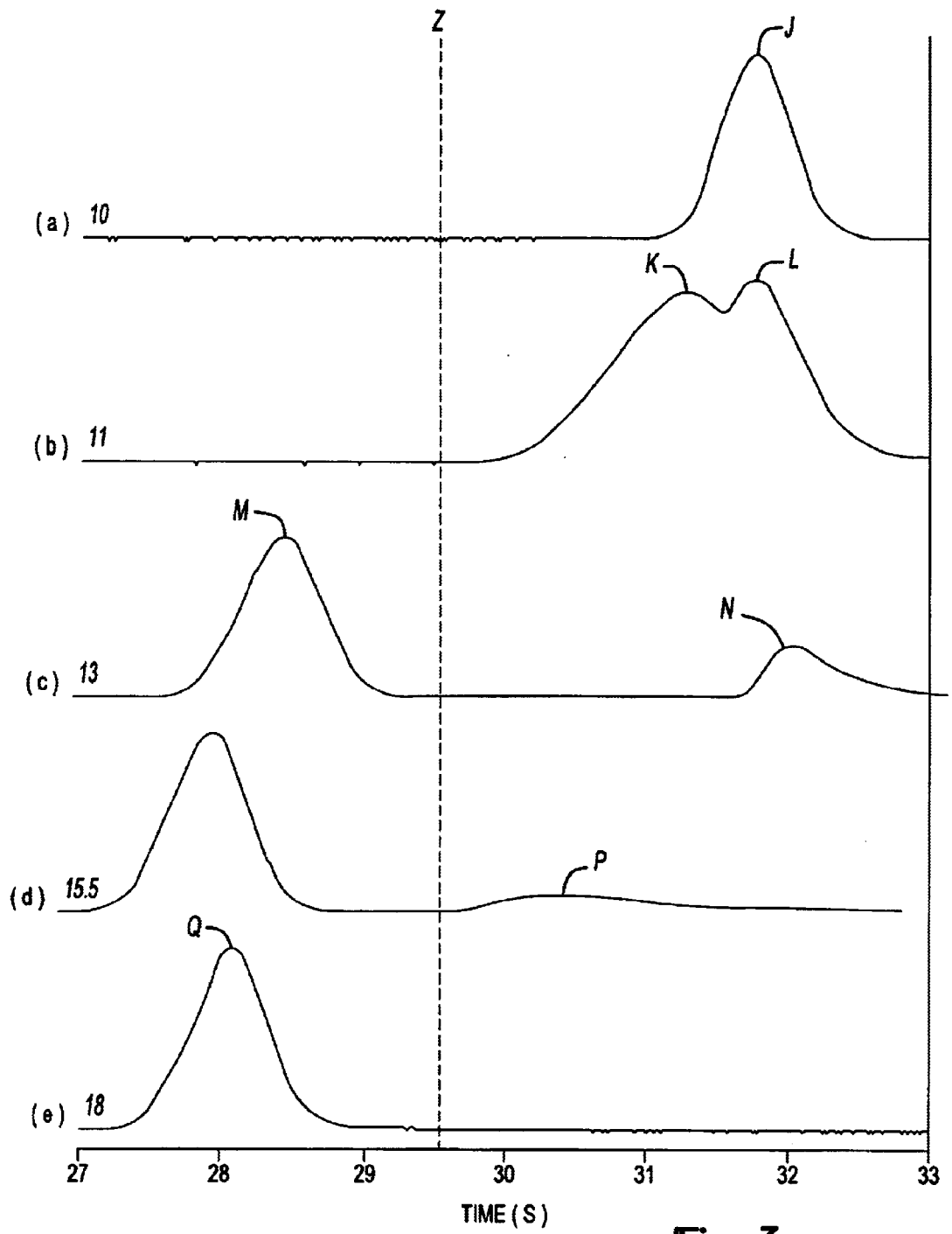
FIGS. 3(*a*)–(*e*) is a series of chromatograms illustrating the result of application of an upward pressurized pulse applied at 10 s, 11 s, 13 s, 15.5 s, and 18 s, respectively, after injection.
Figure 4:
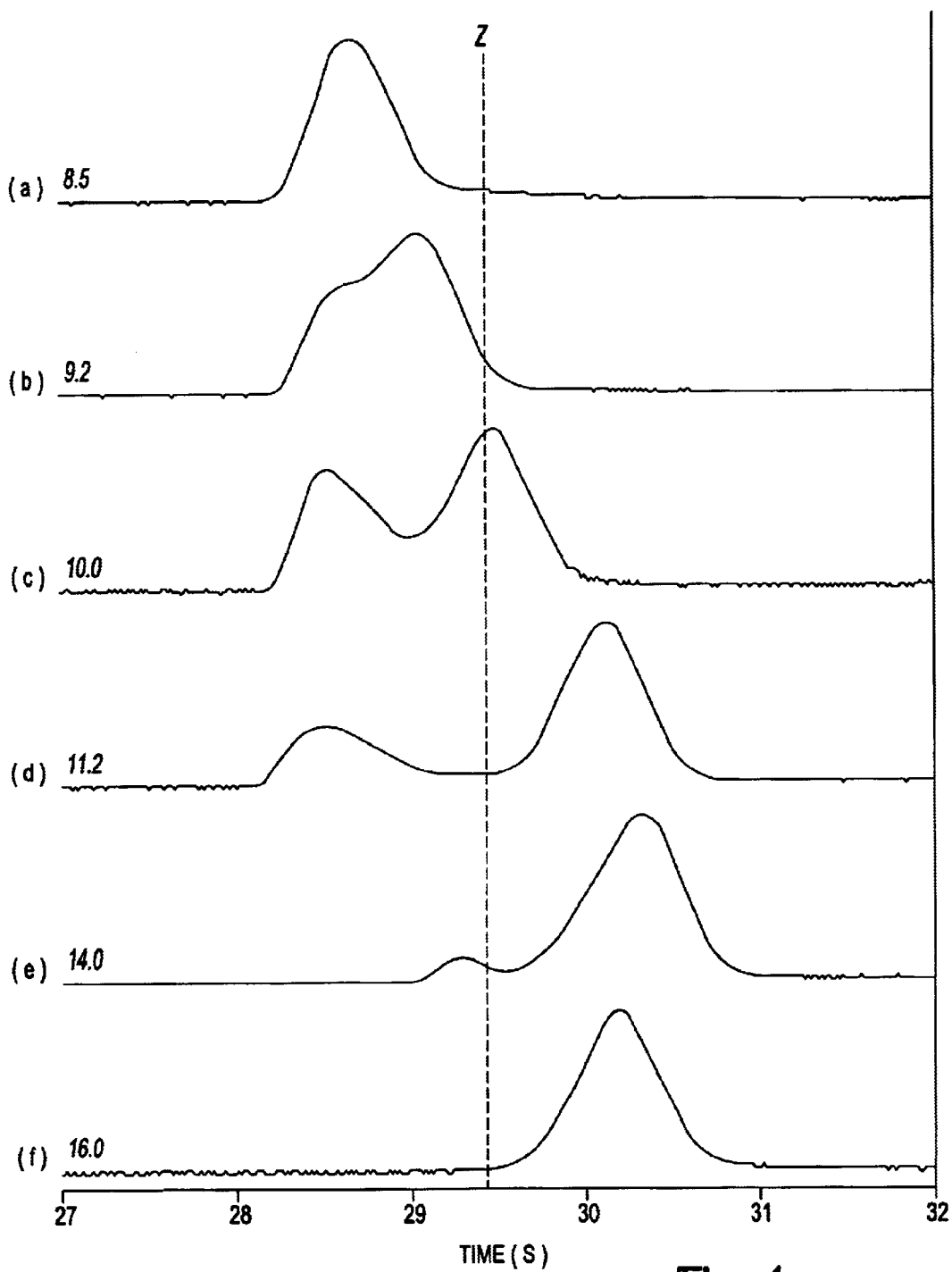
FIGS. 4(*a*)–(*f*) is a series of chromatograms illustrating the result of application of a downward pressurized pulse applied at 8.5 s, 9.2 s, 10.0 s, 11.2 s, 14.0 s, 16.0 s, respectively, after injection.

Referring in particular to FIG. 3(a), a pulse initiation time of 10.0 seconds after analyte mixture injection results in the entire pulse J occurring while both components 100 and 102 are on first column 14. This shifts the apex of peak J to a retention time of approximately 31.8 seconds, but has very little change in the shape of the peak. Referring to FIG. 3(b), when the pressurized pulse initiation time is delayed until 11.0 seconds after injection, both components 100 and 102 are on first column 14 at the beginning of the pressurized pulse, but part of first component 100 crosses column junction point 28 before the end of the pressurized pulse. This results in a broad, distorted double peak K and L.

As seen in FIG. 3(c), with a pulse initiation time of 13.0 seconds, first component 100 has completely crossed column junction point 28 prior to the pressurized pulse and second component 102 remains on first column 14 during the entire duration of the pressurized pulse. This results in a large shift of peak M to lower ensemble retention time for first component 100 and no significant change in retention time for second component 102, illustrated by peak N, relative to the 10.0 second pulse initiation time. The peak-apex separation for the 13.0 second delay case is 3.8 seconds. The peak tailing observed for second component 102 in FIG. 3(c) is often seen for alcohols and is observed even when only this example compound is injected and no pressurized pulse is used.

Referring now to FIG. 3(d), with a 15.5 second pulse initiation time, second component 102 reaches column junction point 28 before the pressurized pulse is complete. Consequently, a very broad, low-amplitude feature P is observed in the chromatogram. As seen in FIG. 3(e), with an 18.0 second pulse initiation time, both components have migrated across column junction point 28 prior to pulse initiation and only a single peak Q is seen in the chromatogram. However, the peak apex retention time has shifted by 1.5 seconds relative to the case with no pressurized pulse.

The same general trends are observed for the downward pressurized pulse illustrated in FIGS. 4(a)–(f), but the retention-time shifts relative to the no-pressure-pulse case (broken vertical line Z) are in the opposite direction. In addition, the maximum peak separation is only 1.8 seconds, compared to 3.8 seconds for the upward pressurized pulse case above. For the no-pressurized-pulse case, the elution times for first column 14 for components 100 and 102 differ by about 4.9 seconds.

Figure 6:
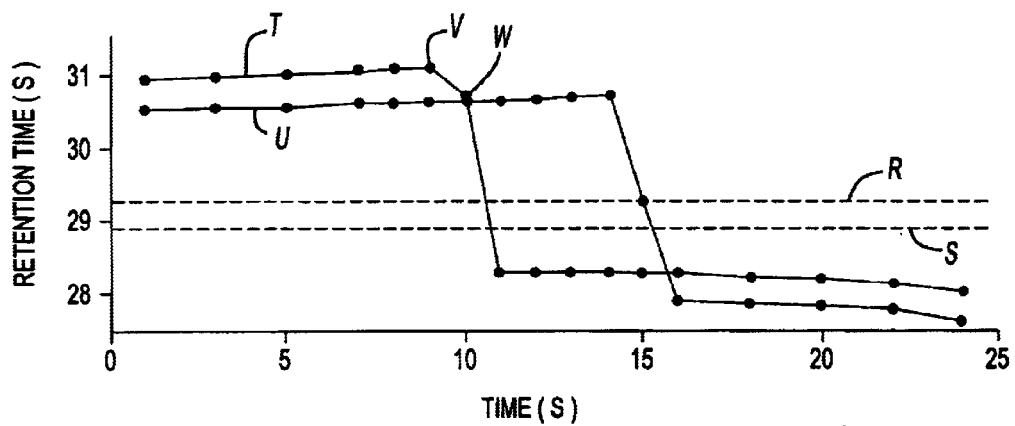
FIG. 6 is a graph illustrating the relationship between ensemble retention-time vs. pulse initiation-time for the pair of illustrative components for an upward pressurized pulse.

FIG. 6 illustrates a graph of ensemble retention-time vs. pulse initiation-time for first component 100 and second component 102 for an upward pressurized pulse with a 3.0 seconds nominal pulse width. A pair of broken horizontal lines R and S illustrate the calculated ensemble retention times for the case of no pressurized pulse for first component 100 and second component 102, respectively. Line T represents first component 100, while line U represents second component 102.

For an upward pressurized pulse, pulse initiation times less than 9 seconds result generally in a constant shift in retention times of about 1.6 seconds for both components since the pressurized pulse is complete before either component reaches column junction point 28. This is illustrated by the relative shift of lines R and T and lines S and U. For pulse initiation times in the range of about 9–11 seconds, first component 100 reaches column junction point 28 before completion of the pressurized pulse, and the retention time for first component 100 sharply decreases at Point V. For pulse initiation times in the range of about 11–14 seconds, the entire pressurized pulse occurs while first component 100 is on second column 16 and second component 102 is on first column 14. Here, a separation of 2.3–2.4 seconds is observed with the higher values occurring near the end of this time interval because of carrier gas acceleration. If the pressurized pulse initiation time is in the range of about 16–24 seconds, both components 100 and 102 are on second column 16 during the entire pressurized pulse and the resultant peaks illustrate nearly equal shifts to shorter retention times. As the pressurized pulse initiation time is further increased, one or both peaks elute from column ensemble 14, 16 before the pressurized pulse is completed and the retention times return to their no–pulse values.

It may be important to note that in FIG. 6, lines T and U cross for a pulse initiation time of about 10 seconds. This is explained by reference to the band migration trajectory plots in FIGS. 2(a)–(f). Without a pressurized pulse, the band trajectories E and F cross just prior to elution from column ensemble 14, 16 with the result that second component 102 elutes from column ensemble 14, 16 about 0.4 seconds before first component 100 as indicated by H'. With an upward pressurized pulse beginning 10 seconds after injection, first component 100 reaches column junction point 28 before the end of the pressurized pulse and its ensemble retention time is shifted lower by about 0.4 seconds. This results in complete co-elution of the two components at point W. Further delay in the start of the pressurized pulse by 1 second results in a larger shift for first component 100, resulting in an elution-order change and a relatively large separation.

Figure 7:
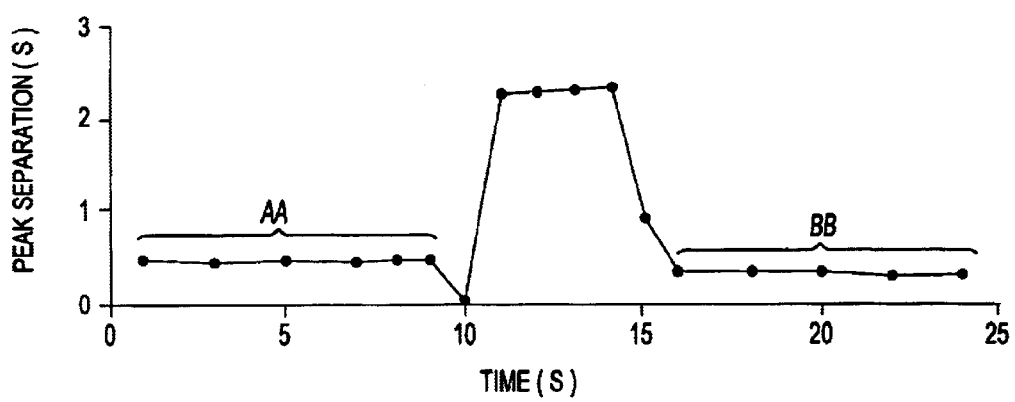
FIG. 7 is a graph illustrating the relationship between peak separations vs. pulse initiation-time for the pair of illustrative components for an upward pressurized pulse.

Similarly, FIG. 7 illustrates a graph of ensemble peak separation vs. pulse initiation-time for first component 100 and second component 102 for an upward pressurized pulse with a 3.0 seconds nominal pulse width. Peak separation with no pressurized pulse is about 0.4 seconds as shown by the separation of lines R and S in FIG. 6. The nearly flat regions, generally indicated at AA and BB, are expected from the retention time plots in FIG. 6. The maximum predicted peak separation for the upward pressurized pulse illustrated in FIG. 7 is about 2.4 seconds, while measured peak separations are about 3.8 seconds.

Figure 8:
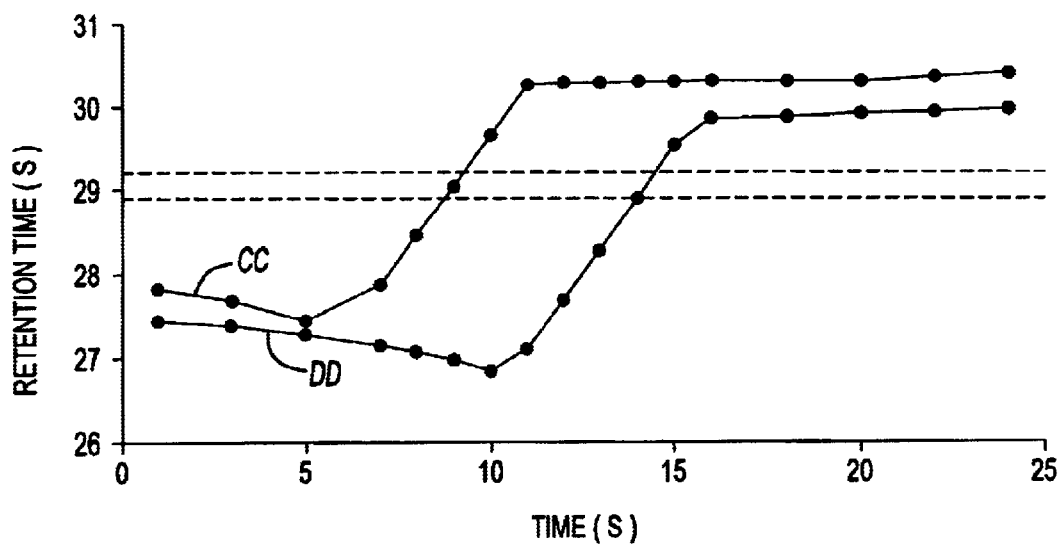
FIG. 8 is a graph illustrating the relationship between ensemble retention-time vs. pulse initiation-time for the pair of illustrative components for a downward pressurized pulse.

FIG. 8 is similar to FIG. 6 except the data is for the case of a downward pressurized pulse with a nominal width of 3.0 seconds, rather than an upward pressurized pulse. Line CC represents first component 100, while line DD represents second component 102. For the downward pressurized pulse with initiation times less than about 4 seconds, the entire pulse is complete before either components 100 or 102 reaches column junction point 28 and the retention times decrease only slightly in this interval with increasing delay in the pressurized pulse initiation. For pulse initiation times in the range of about 4–10 seconds, first component 100 reaches column junction point 28 prior to completion of the pressurized pulse. Consequently, its ensemble retention time increases with increasing initiation time due to the lower carrier gas velocity on second column 16 during the pressurized pulse. Second component 102 reaches column junction point 28 in about 10 seconds, and for pulse initiation times greater than about 10 seconds, the ensemble retention time for second component 102 increases rapidly with increasing pulse initiation time until about 16 seconds when second component 102 crosses column junction point 28. Further increases in pulse initiation time have only a minor effect on retention times until about 26 seconds when components 100 and 102 begin to elute from column ensemble 14, 16 before completion of the pressurized pulse. For pulse initiation times greater than about 30 seconds, both components elute prior to the start of the pressurized pulse and the retention times are the same as the no-pulse values.

As can be seen in FIG. 8, lines CC and DD do not cross as in the case illustrated in FIG. 6. In other words, a downward pressurized pulse causes the retention time for first component 100 to shift to larger values for pulse initiation times greater than five seconds. There is no change in elution order and thus lines CC and DD do not cross. It is interesting to note that the shift in ensemble retention times for first component 100 occurs for initiation times greater than 8 seconds for the upward pressurized pulse (see FIG. 6) and for times greater than 5 seconds for the downward pulse (see FIG. 8). This is the result of the lower carrier gas velocity on first column 14 during an upward pulse and the higher carrier gas velocity on first column 14 during a downward pulse.

Figure 9:
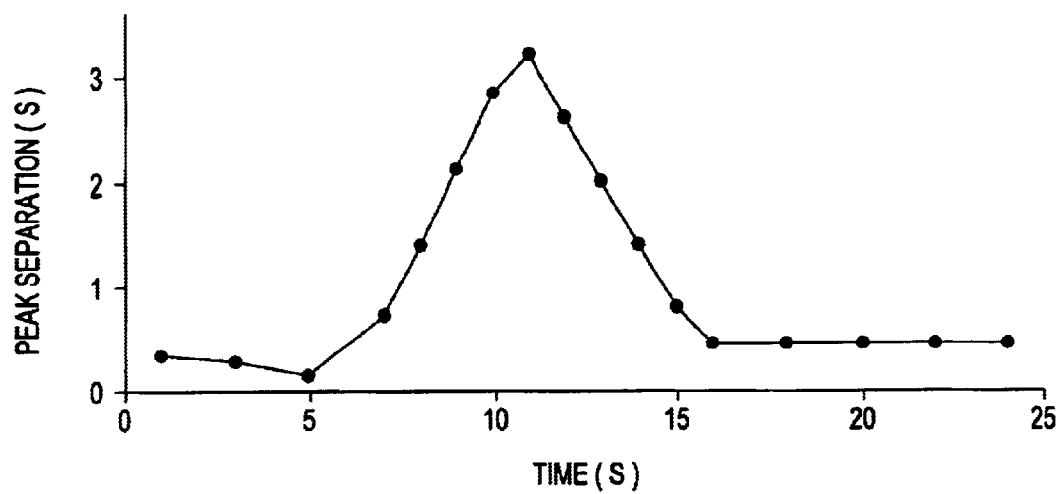
FIG. 9 is a graph illustrating the relationship between peak separations vs. pulse initiation-time for the pair of illustrative components for a downward pressurized pulse.

Referring now to FIG. 9, the triangularly shaped peak-separation vs. pulse-initiation-time plot for the downward pressurized pulse is the result of the increased carrier gas velocity on first column 14 during the pressurized pulse. This causes second component 102 to begin shifting to larger retention time values for pulse initiation times greater than 10 seconds; while component 100 has not completely shifted to higher values for initiation times less than 11 seconds. For the downward pressurized pulse, the maximum predicted peak separation as seen in FIG. 9 is about 3.3s, while measured peak separations is about 1.7 seconds. These differences between the predicted and observed maximum peak separation values are due in part to the pressurized pulse shapes illustrated in FIGS. 4(a) and (b).

Figure 10:
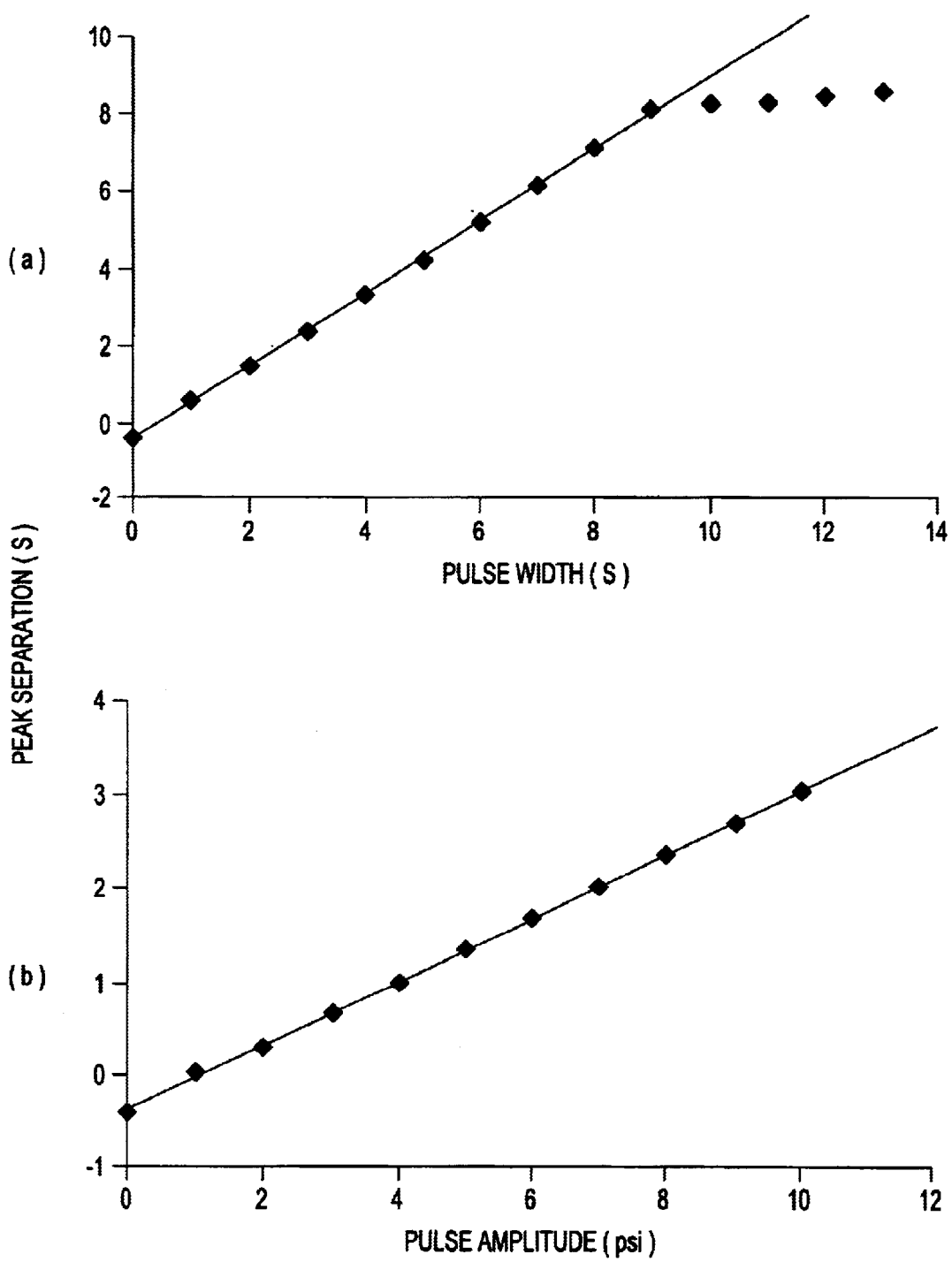
FIG. 10(a) is a graph illustrating the relationship between peak separation vs. pressurized pulse width for the pair of illustrative components.
FIG. 10(b) is a graph illustrating the relationship between peak separations vs. pressurized pulse amplitude for the pair of illustrative components.

FIGS. 10(a) and (b) illustrates the effect on peak separation caused by changes in the pressurized pulse width Δt and amplitude ΔP for the case of an upward pressurized pulse, respectively. With particular reference to FIG. 10(a), ΔP is held constant at 8.0 psi. Similarly, with reference to FIG. 10(b), Δt is held constant at 3.0 seconds. For both FIGS. 10(a) and (b), the pressurized pulse initiation time is 12 seconds such that first component 100 has crossed column junction point 28 but second component 102 is still on first column 14 at the start of the pressurized pulse.

Referring now to FIG. 10(a), for pulse widths up to about 9.0 seconds, the peak separation is nearly linear with varying pulse width. For pulse widths greater than 9.0 seconds, second component 102 crosses column junction point 28 prior to the end of the pressurized pulse and, thus, has little effect on peak separation.

Referring now to FIG. 10(b), it can be seen that peak separation vs. pulse amplitude remains generally linear for the amplitude range 2–10 psi. Therefore, because of the peak separation being proportional to the pressurized pulse amplitude and width, the peak separation should be proportional to the pressurized pulse area (ΔPΔt).

According to the principles of the present invention, a gas chromatography system is provided that employs relatively narrow pressurized pulses to control the separation of specific or discrete pair of components eluting from a column ensemble 14, 16. For mixture components that are on the same column during the pressurized pulse, little change in peak pattern and peak-pair separation occurs in the ensemble chromatogram. However, relatively large peak separation increases are observed only when one of the pair of mixture components is on second column 16 and the other of the pair of mixture components is still on first column 14 during at least a portion of the pressurized pulse. The principles of the present invention are particularly useful for complex mixtures where most components are adequately separated, yet it is necessary to obtain enhanced separations for a relatively few component pairs or small groups without loosing separation quality for the rest of the mixture components. This approach also may be more useful than pressure (selectivity) tuning and programming since for most of the duration of the analysis the quiescent pressure at column junction point 28 can be adjusted to give minimum ensemble void time. It is important to note that instead of applying a set pressure at the column junction point, which would invariably cause other previously separated component pairs to now co-elute, the present invention applies a brief pressurized pulse at an optimal time to cause a targeted pair of components to elute separately without adversely effecting the remaining components in the mixture.

Furthermore, it has been shown that upward pressurized pulses may be more useful than downward pulses for several reasons. First, an upward pressurized pulse results in a decrease in the carrier gas velocity on first column 14, and this increases the available time for the pressurized pulse to be completed before the second component reaches the junction. Second, a downward pressurized pulse is more likely to result in sample loss through the vent line if the pressure during the pressurized pulse falls below the pressure that would exist at column junction point 28 in the absence of the pressure controller. Third, the pressure equilibration time is smaller for an upward pulse for any specified quiescent-pressure value. However, downward pressurized pulses do have some useful applications.

According to a second embodiment of the present invention, a method and apparatus are provided for achieving improved selectivity for gas chromatography with capillary columns. This second embodiment replaces electronic pressure controller 22 of the first embodiment with a low-volume gas valve coupled between column junction point 28 and an atmospheric pressure vent line.

As described in detail above, electronic pressure controller 22 of gas chromatography system 10 is used to change the pressure at column junction point 28 for a predetermined time interval and then return the pressure to its original value. This pressure change, when timed correctly, enhanced the ensemble separation of first component 100 and second component 102. However, electronic pressure controller 22 may not afford sufficiently rapid pressure equilibration time. This can be seen in FIGS. 5a and 5b in the curves inability to follow the ideal square pressure pulse. That is, electronic pressure controller 22 of the first embodiment defines an internal volume of greater than approximately 7 cm$^3$. Therefore, this internal volume may result in an excessive equilibration time, which may preclude pressure pulses of less than about 5 seconds in width. This may not be of importance in some applications, however it may be useful to use pressure pulses of less than 5 seconds in certain separation applications.

Figure 11:
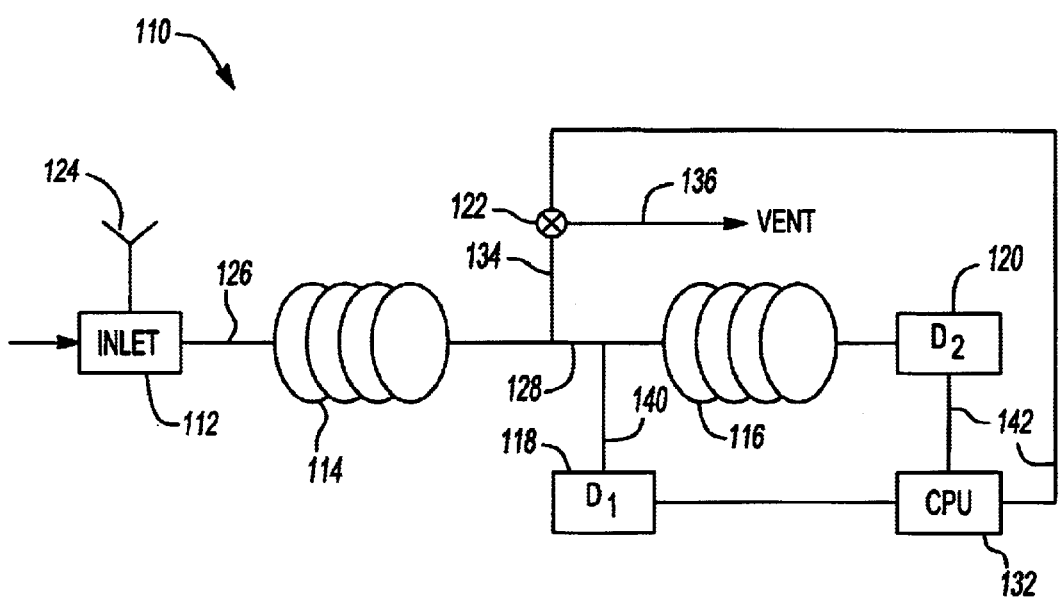
FIG. 11 is a schematic drawing illustrating a gas chromatography system according to a second embodiment of the present invention.

According to the principles of the second embodiment, electronic pressure controller 22 and carrier gas supply 30 are eliminated and replaced with a lower cost, low-volume gas valve coupled between a column junction point 128 and an atmospheric pressure vent line 136. With particular reference to FIG. 11, a pressure-controlled, dual-column, gas chromatography system is schematically illustrated in accordance with a second embodiment of the present invention, generally indicated at 110. Gas chromatography system 110 generally includes an inlet system 112, a first gas chromatography separation capillary column 114, a second gas chromatography capillary column 116, a first detector ($D_1$) 118, a second detector ($D_2$) 120, and an vent valve 122.

Inlet system 112 is configured generally to receive a sample "plug" of an analyte mixture for analysis within gas chromatography system 110. More particularly, a stream of carrier gas from a carrier gas supply 124 entrains such analyte mixture during injection. This entrained analyte mixture and carrier gas composite is introduced into first column 114 through a passage 126. Various configurations of inlet system 112 can be provided, such as mechanical injection valves, cryofocusing systems, and the like.

First column 114 and second column 116 are coupled in series along column junction point 128. Vent valve 122 is fluidly coupled to column junction point 128. Vent valve 122 is preferably a pneumatically operated, low-dead-volume device, which is operated by a 50–55 psig compressed air source connected through an electronically actuated solenoid valve. Atmospheric pressure vent line 136 is provided in fluid connection with vent valve 122 to relieve fluid pressure at column junction point 128 in accordance with the principles of the present invention. Preferably, vent valve 122 is driven in response to a central processing unit 132. Moreover, vent valve 122 is preferably coupled to column junction point 128 via an approximately 4.0 cm long, 0.53 mm diameter (id) deactivated, fused-silica tube 134.

Figure 12:
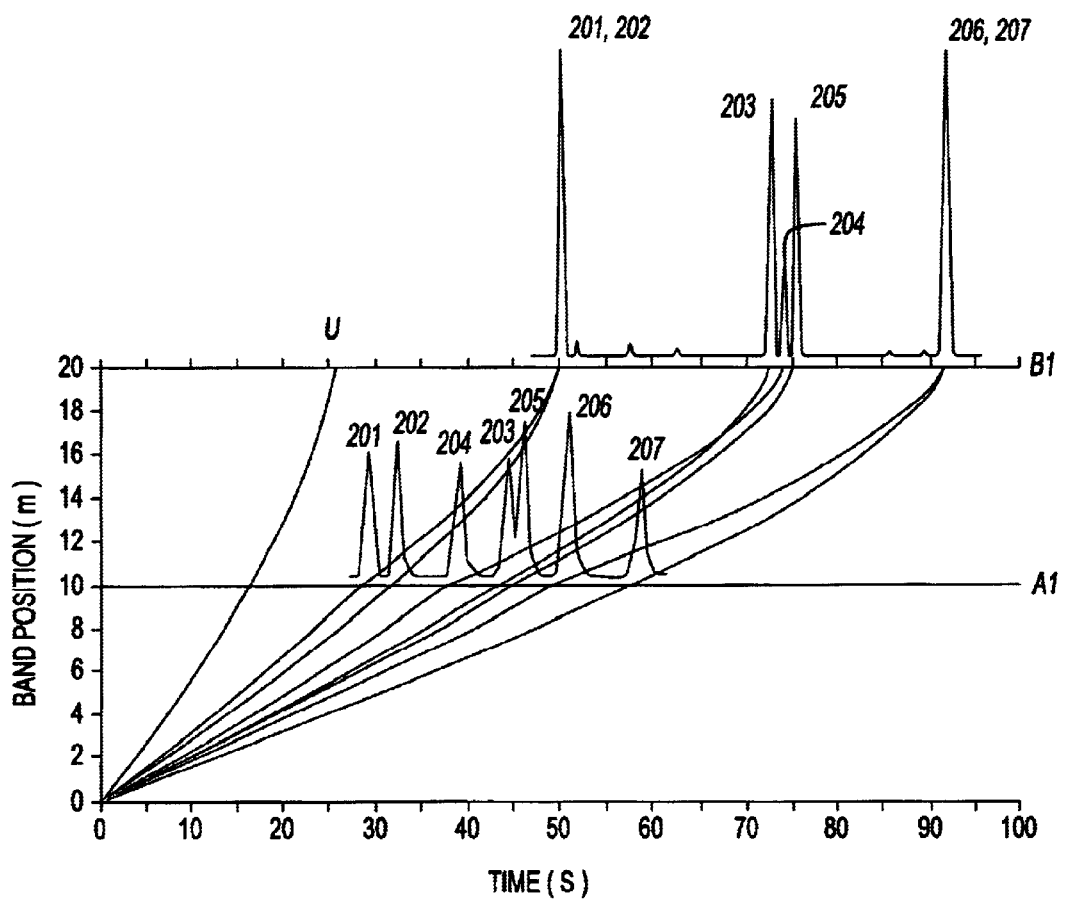
FIG. 12 is a graph illustrating solute band positioning at the column junction point and at the exit of the column ensemble for the case where no pressure pulse is present (e.g. valve closed)

Referring now to FIG. 12, the retention characteristics of a test mixture on gas chromatography system 110 is illustrated for a case in which vent valve 122 is closed during the entire separation sequence. This figure illustrates plots of the positions of the solute bands in the ensemble as a function of time, wherein line A1 represents the solute band position at column junction point 128 and line B1 represents the resultant solute band position at the exit of second column 116.

The seven components, as indicated by 201, 202, 203, 204, 205, 206, and 207 were chosen for purposes of discussion to yield closely spaced groups of peaks in the ensemble chromatogram under conditions when vent valve 122 is closed during the entire separation. It is important to note that components 201 and 202, and 206 and 207 are separated by first column 114, but coelute from second column 116. On the other hand, component 204 is well-separated from components 203 and 205 by first column 114, but an elution order change occurs for components 203 and 204 on second column 116, with the result that peaks 203 and 204 are not completely separated by second column 116.

Referring now to FIGS. 13(a)–(g), a chromatogram is illustrated for components 203, 204, and 205 when vent valve 122 is opened for various time intervals (nominal pulse width) beginning 41 seconds after injection. The values to the right of each figure give the nominal open time for vent valve 122 in seconds. When the valve is initially opened, component 204 has migrated across column junction 128 and is in second column 116, while components 203 and 205 are still on first column 114. When vent valve 122 is opened, the pressure at column junction point 128 falls from 21.0 psia to ambient pressure (14.2 psia). As one skilled in the art will understand, the pressure at column junction point 128 is the outlet pressure for first column 114 and the inlet pressure for second column 116. Thus, when vent valve 122 is open, the local carrier gas velocity at any point in first column 114 is increased, and the local carrier gas velocity in second column 116 is decreased. The result is an increased migration rate in first column 114 and a decreased rate in second column 116 for the interval when vent valve 122 is open. This shifts the ensemble retention time for component 204, which is in second column 116 when vent valve 122 is open, to larger values and shifts the retention times for components 203 and 205 to smaller values.

Figure 13:
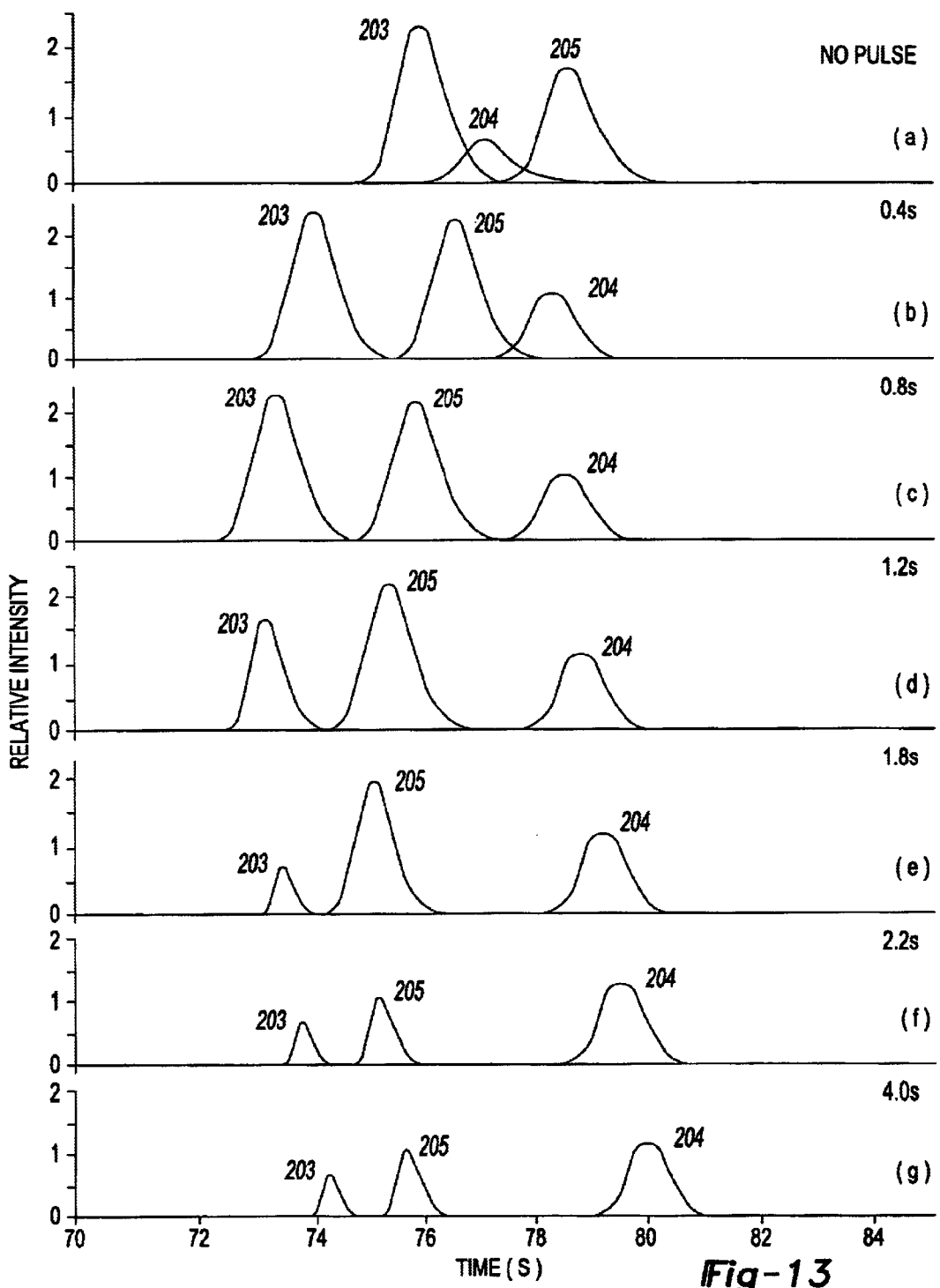
FIGS. 13(a)–(g) is a series of chromatograms illustrating the result of application of differing nominal pulse widths of 0 s (no pulse), 0.4 s, 0.8 s, 1.2 s, 1.8 s, 2.2 s, and 4.0 s, respectively.

With particular reference to FIG. 13(b), a nominal pulse width of 0.4 seconds results in an elution order change for components 204 and 205. While, a pulse width of 0.8 seconds results in baseline separation of all components 203, 204, and 205, as seen in FIG. 13(c). Further increase in the pulse width to 1.2 seconds results in increased separation of components 204 and 205, but a decrease in area is observed for peak 203. For a nominal pulse width of 1.8 seconds, the area of peak 203 is reduced to approximately 12% of the no-pulse value, and the area of peak 205 illustrates a significant decrease. The decreases in peak area are the result of venting some of the sample through vent valve 122 and atmospheric vent line 136. The amount of sample that is vented increases with pulse width until the width is sufficient that the residual sample crosses the junction and the venting ceases, as can be seen by the decrease in component peak widths when venting occurs. This has been explained by a decrease in the elution peak width from first column 114 when the carrier gas velocity in first column 114 is increased during the pulse.

Still referring to FIGS. 13(a)–(g), the chromatograms suggest that a nominal pulse width between 0.4 and 0.8 seconds will provide adequate separation of components 203, 204, and 205 with minimal component venting. The effects of pulse width on peak separation and peak area for components 203, 204, and 205 are shown in greater detail in FIGS. 14(a) and (b). That is, with no pulse (pulse width of 0 seconds), the peak separation of component pair 204/205 is approximately—1.4 seconds and that of component pair 203/204 is just over about 1 second. The negative value for the peak separation of component pair 204/205 with no pulse is the result of the ensemble elution order change when vent valve 122 is opened. Neither value is adequate for a complete baseline separation. For a nominal pulse width between 0.5 and 1.2 seconds, all component pairs have separations greater than 2 seconds, which provides better than baseline separation.

Figure 14:
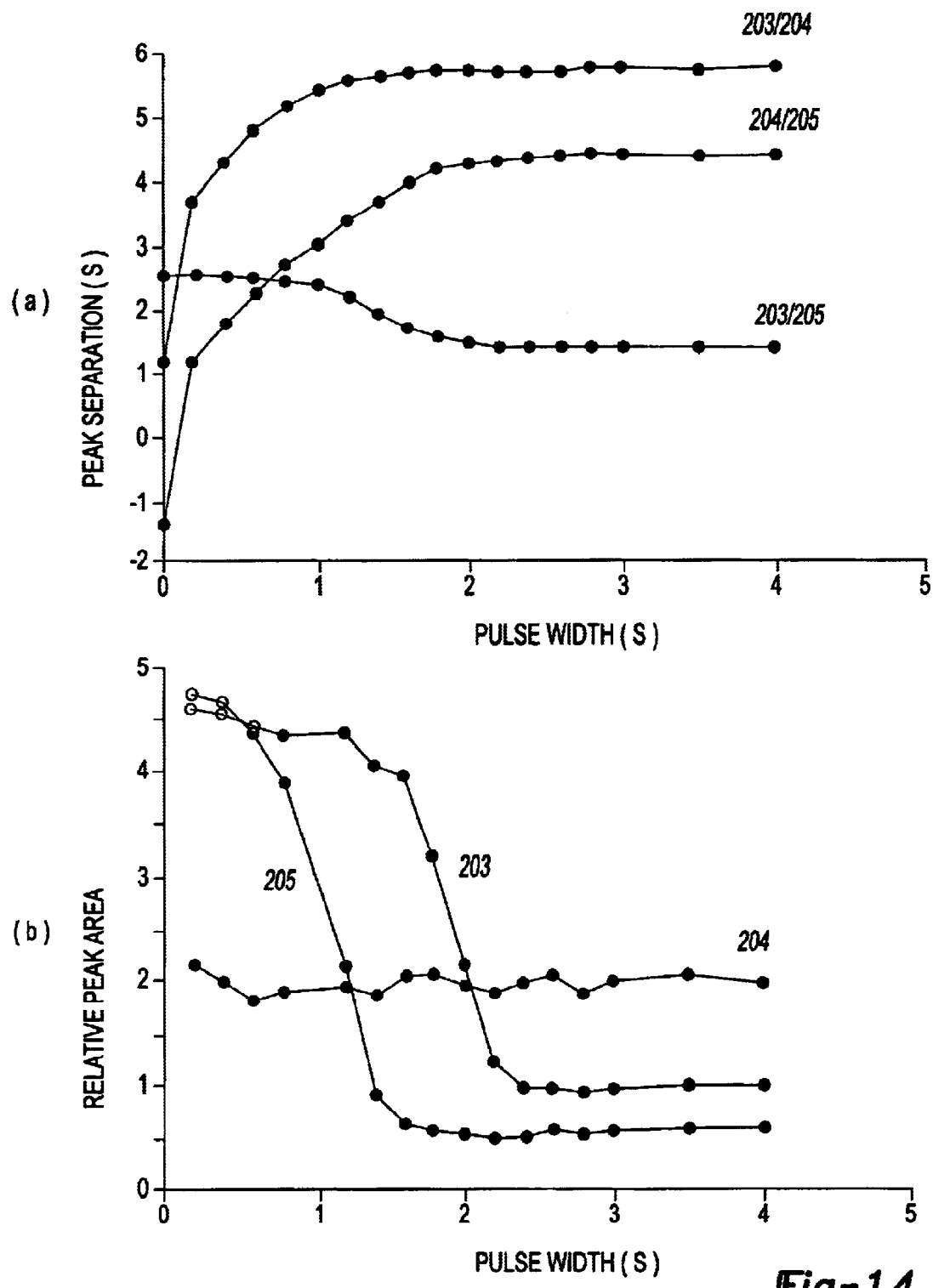
FIG. 14(a) is a graph illustrating the effects of pulse width on peak separation between component pairs 203/204, 204/205, and 203/205.
FIG. 14(b) is a graph illustrating the effects of pulse width on the relative peak area for components 203, 204, and 205.

Referring now to FIG. 14(b), the relative peak area plots show that for component 204, the peak area is independent of the pulse width. This is expected, because component 204 has crossed the junction before the pulse is initiated. For components 203 and 205, a sharp loss in peak area is observed if the corresponding components reach column junction 128 prior to the time that vent valve 122 closes. For component 205, which reaches column junction 128 before component 203 (see FIG. 12), the nominal pulse width should not exceed approximately 0.5 seconds in order to obtain minimal component venting. Because a nominal pulse width of 0.5 seconds provides adequate separation of components 203, 204, and 205, this value was used below for discussion purposes.

Figure 15:
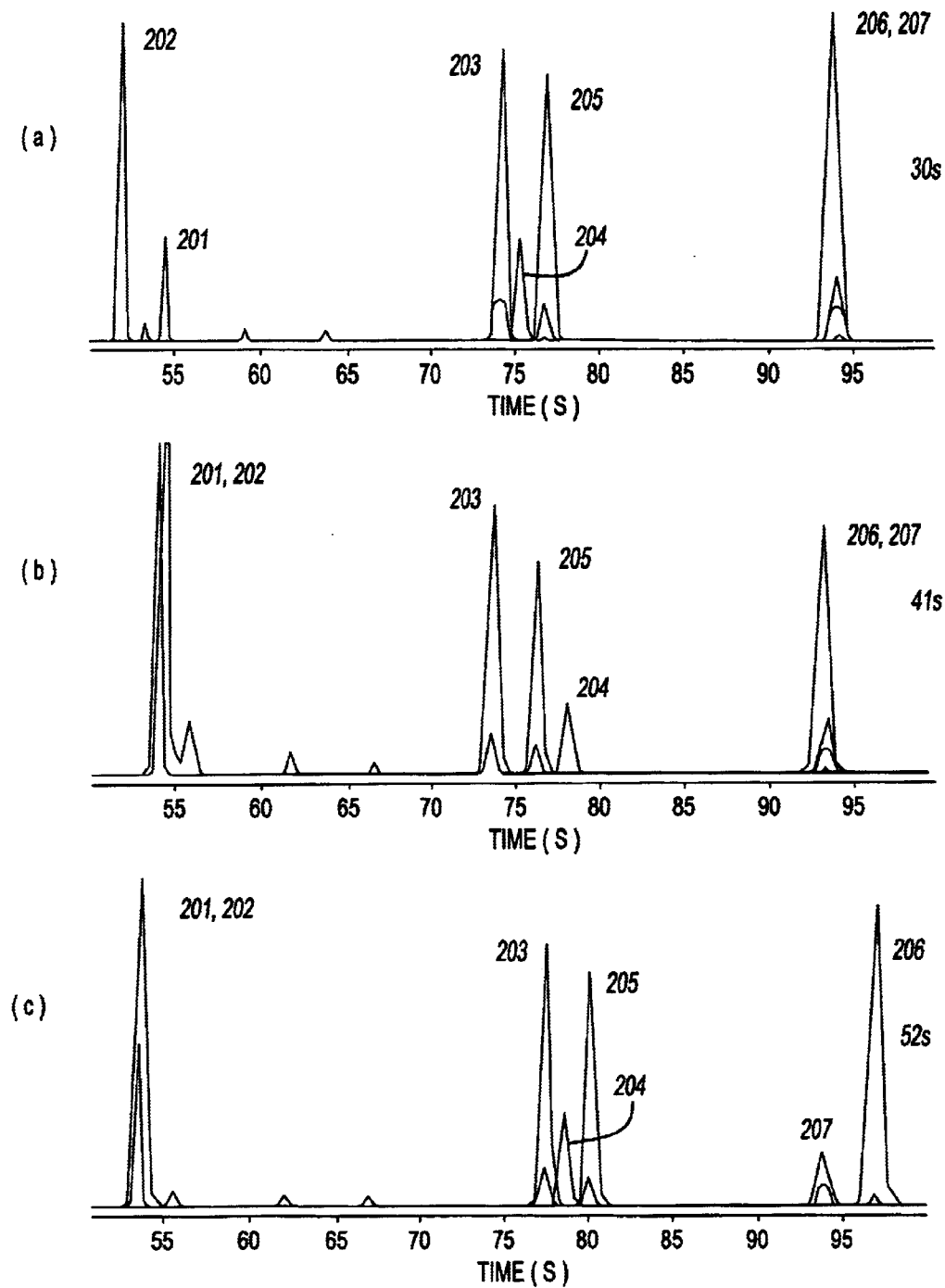
FIGS. 15(a)–(c) is a series of chromatograms illustrating the result of application of a pulse applied at 30 s, 41 s, and 52 s, respectively, after injection.

FIGS. 15(a)–(c) illustrates extracted-ion chromatograms from the complete mixture for a single 0.5 second wide pulse initiated at (a) 30 seconds, (b) 41 seconds, and (c) 52 seconds after injection, respectively. Note that in addition to the seven mixture components, several small impurity peaks also are observed in the extracted-ion chromatograms. When the pulse is initiated 30 seconds after injection as seen in FIG. 15(a), components 201 and 202 are well-separated, but component groups 203/204/205 and 206/207 show no significant change in the ensemble peak patterns relative to the no-pulse case. For a pulse initiation time of 41 seconds, a complete separation of components 203, 204, and 205 is achieved, but coelutions are observed for component pairs 201/202 and 206/207. For a pulse initiation time of 52 seconds, component pair 206/207 is well-separated, but the pattern of peaks for component groups 201/202 and 203/204/205 are essentially the same as for the no-pulse case.

Figure 16:
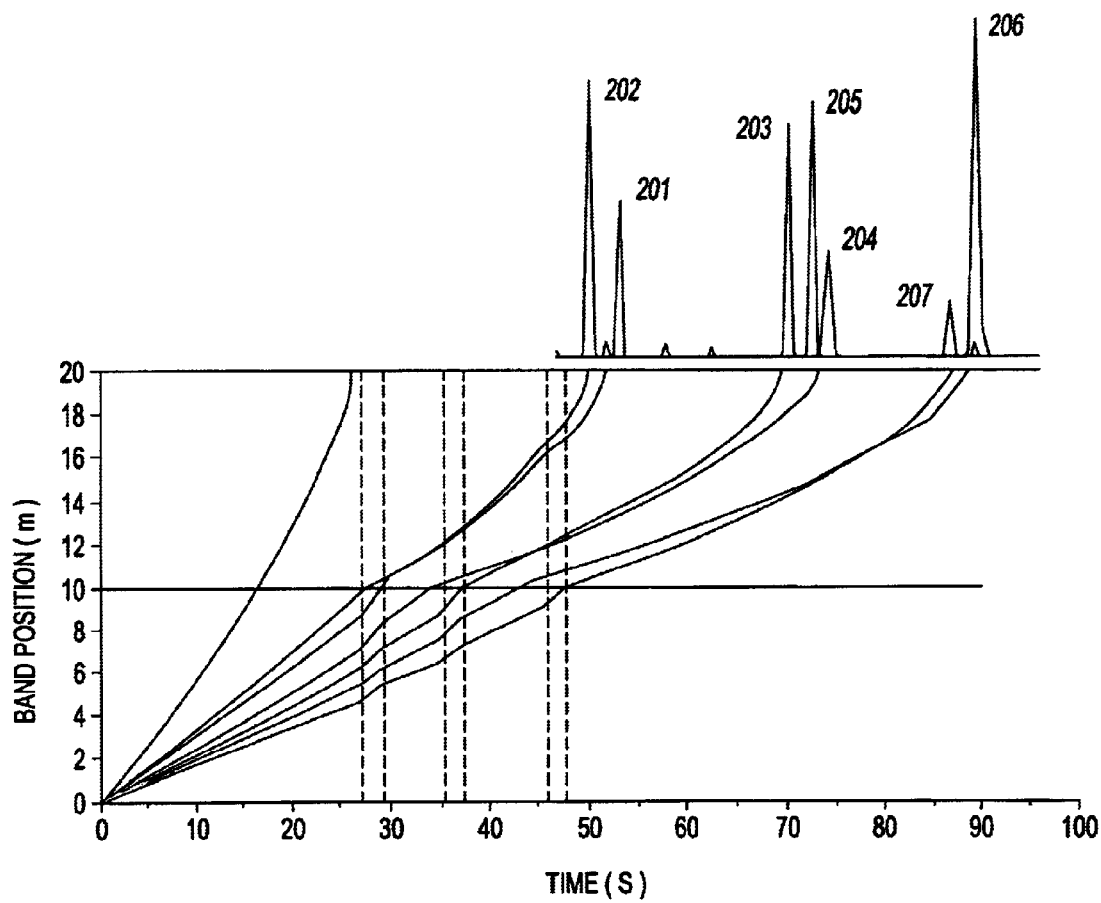
FIG. 16 is a graph illustrating solute band positioning at the column junction point and at the exit of the column ensemble for the case where the vent valve is opened at three distinct times to create three distinct pulses.

Therefore, it can be seen that the test mixture used in this example results in three congested regions of the ensemble chromatogram. Accordingly, as seen in FIG. 16, a sequence of three pulses can be used to improve the separation of all three of the groups of mixture components. The broken vertical lines indicate the required pulse initiation times and duration. It is important to note, however, that the required pulse-initiation times are altered by any previously applied pulses, because each previously applied pulse reduces the time required for subsequent component groups to reach column junction 128. This can be taken into account by using an algorithm to determine the band position vs time plots or, alternatively, by monitoring first column 114 using first detector 118 to determine the appropriate pulse initiation times.

Figure 17:
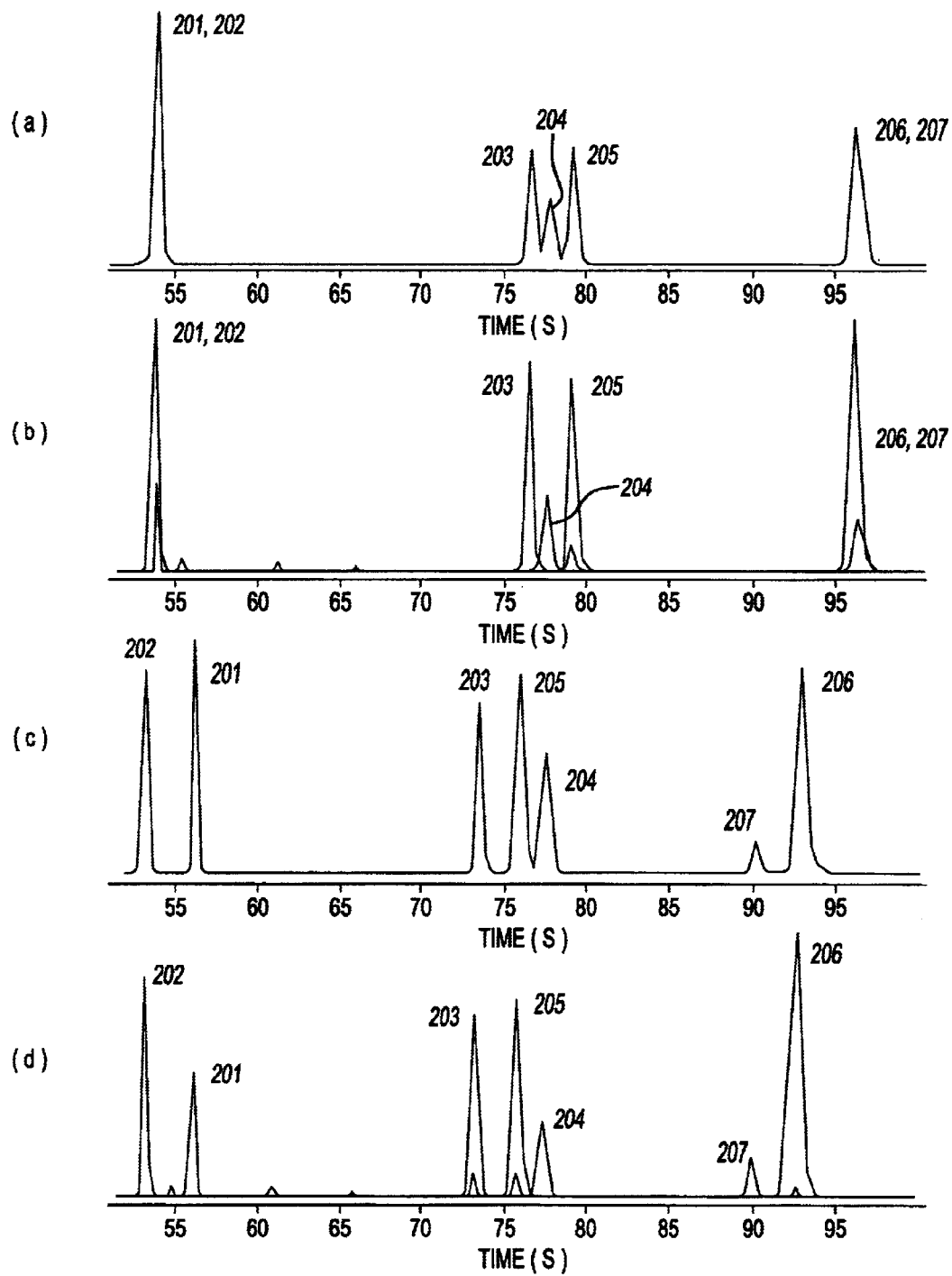
FIG. 17(a) is an analytical-ion chromatogram (AIC) illustrating the case where no pulse is applied.
FIG. 17(b) is an extracted-ion chromatogram (EIC) illustrating the case where no pulse is applied.
FIG. 17(c) is an analytical-ion chromatogram (AIC) illustrating the case where three pulses are applied.
FIG. 17(d) is an extracted-ion chromatogram (EIC) illustrating the case where three pulses are applied.

FIGS. 17(a)–(d) illustrate a direct comparison of the analytical ion chromatograms (AIC) (FIGS. 17(a) and (c)) and extracted-ion chromatograms (EIC) (FIGS. 17(b) and (d)) for the no-pulse case (FIGS. 17(a) and (b)) and for the case when three sequential 0.5 second (nominal) pulses are used as described in FIG. 16 (FIGS. 17(c) and (d)). The analytical ion chromatograms are obtained by summing all the extracted ion chromatograms that exceed a user-defined signal-to-noise ratio for the found peaks. The analytical ion chromatograms provide information that is similar to that obtained in a total-ion chromatogram but at substantially increased signal-to-noise ratios. For this work, the analytical ion chromatograms are used to simulate the use of a single-channel detector, such as an flame ionization detector.

With particular reference to FIGS. 17(a) and (b) where no pulse is applied, the analytical ion chromatogram illustrates only five peaks as a result of the overlap of component pairs 201/202 and 206/207. In addition, the peaks of components 203 and 204 show excessive overlap, which prevents accurate peak-area calculations. As seen in FIGS. 17(c) and (d), when three pulses are applied by vent valve 122, the analytical ion chromatogram illustrates that a complete separation is achieved with at least baseline resolution for all adjacent components.

As should be appreciated from the foregoing discussion in connection with the second embodiment of the present invention, the use of a low-dead-volume valve 122 and an atmospheric pressure vent 136 can be very effective in enhancing the ensemble separation of specified groups of mixture components. Furthermore, the present invention provides a simple and convenient method of controlling the selectivity in relatively small, specified regions of the ensemble chromatogram. As described in connection with the first embodiment, the second embodiment provides that all of the mixture components that are on the same column during the time that vent valve 122 is open (pulse duration) will be shifted to larger or smaller retention times, but the pattern of peaks for these components from the output second column 116 will be relatively unaffected by the pressure pulse. Lastly, gas chromatography system 110 of the present embodiment provides simpler, less expensive, more flexible method of enhancing the selectivity for series coupled, gas chromatography column ensembles, and further provides a faster pulse response than that provided by the first embodiment of the present invention.

Still further, it was seen that for cases in which more than one coeluton occurs, multiple pulses can be used with each pulse, timed to facilitate the separation of a specified component group. The initiation times of the second and subsequent pulses, however, must be adjusted to take into account the reduced component migration times on first column 114 that are caused by each successive pulse. It should be understood that although the apparatus described herein used isothermal gas chromatography, multiple-pulse techniques should be very effective with temperature-programmed gas chromatography, since the higher-boiling-point mixture components migrate very slowly during the early, low-temperature portion of the analysis, and thus, will be relatively unaffected by pulses that are used to facilitate the separation of the lower-boiling-point components.

An important advantage of the use of short pressure pulses which target specific component groups is that, for most of the analysis time, the column ensemble is operated with vent valve 122 closed, and the column junction-point pressure is the value that would occur without any additional connection to column junction 128. This can substantially increase analysis speed and ensemble efficiency relative to a pressure-tunable column ensemble where the best separation may occur for a junction-point pressure producing larger holdup time and reduced resolving power.

According to a third embodiment of the present invention, a method and apparatus are provided for achieving improved selectivity for gas chromatography with capillary columns. This third embodiment replaces electronic pressure controller 22 of the first embodiment with a pneumatically actuated valve connected between the column junction point and a ballast chamber containing carrier gas at a predetermined pressure sufficient to stop the flow in the first column. However, in the interest of brevity, like features and functions of previous embodiments will not be discussed.

Figure 18:
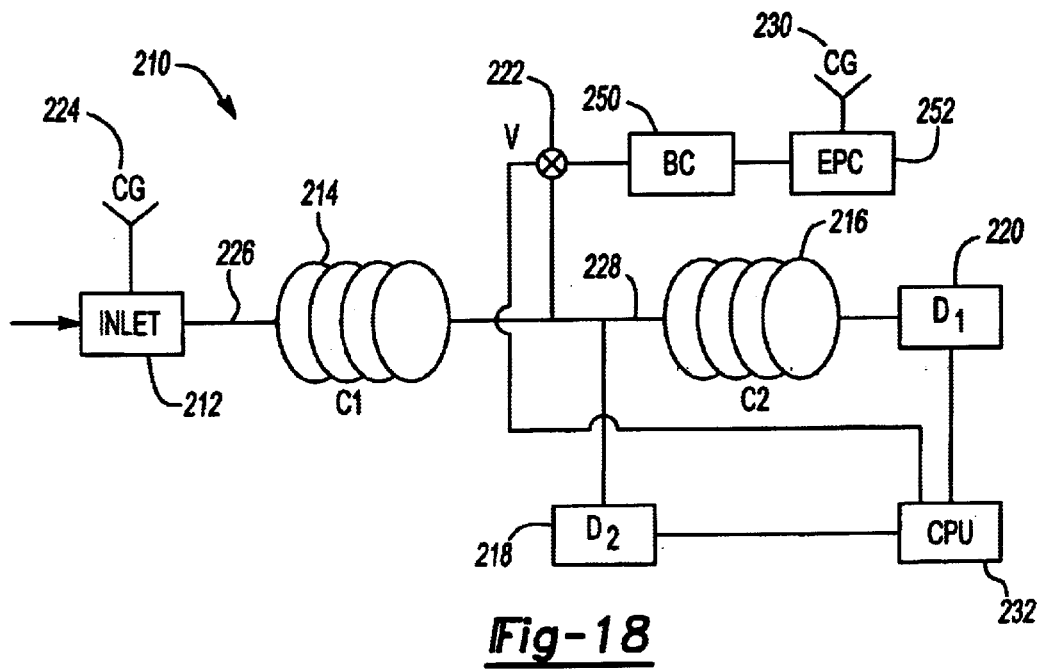
FIG. 18 is a schematic drawing illustrating a gas chromatography system according to a third embodiment of the present invention.

According to the principles of the third embodiment, a low cost, low-volume gas valve 222 is coupled between a column junction point 228 and a ballast chamber 250. Ballast chamber 250 is maintained at a predetermined pressure via a pressure controller 252 and an adjustable pressure source carrier gas supply 230. With particular reference to FIG. 18, a pressure-controlled, dual-column, gas chromatography system is schematically illustrated in accordance with a third embodiment of the present invention, generally indicated at 210. Gas chromatography system 210 generally includes an inlet system 212, a first gas chromatography separation capillary column 214, a second gas chromatography capillary column 216, a first detector ($D_1$) 218, a second detector ($D_2$) 220, and gas valve 222.

Inlet system 212 is configured generally to receive a sample "plug" of an analyte mixture for analysis within gas chromatography system 210. More particularly, a stream of carrier gas from a carrier gas supply 224 entrains such analyte mixture during injection. This entrained analyte mixture and carrier gas composite is introduced into first column 214 through a passage 226. Various configurations of inlet system 212 can be provided, such as mechanical injection valves, cryofocusing systems, and the like.

First column 214 and second column 216 are coupled in series along column junction point 228. Gas valve 222 is fluidly coupled to column junction point 228. Gas valve 222 is preferably a pneumatically operated, low-dead-volume device, which is operated by a 50–55 psig compressed air source connected through an electronically actuated solenoid valve. Ballast chamber 250 is provided in fluid connection with gas valve 222 to provide or produce fluid pressure or pulse at column junction point 228 in accordance with the principles of the present invention. Preferably, gas valve 222 is driven in response to a central processing unit 232. Moreover, gas valve 222 is preferably coupled to column junction point 228 via an approximately 4.0 cm long, 0.1 mm diameter (id) deactivated, fused-silica tube 234.

As discussed above in regard to the first embodiment, electronic pressure controller 22 may not afford sufficiently rapid pressure equilibration time. This can be seen in FIGS. 5a and 5b where the curves do not follow an ideal square pressure pulse. Although this may not be an issue in all applications, in those that require near ideal pressure pulses, it has been determined that the use of ballast chamber 250 is capable of providing the necessary pulse profile in many cases due to its larger volume.

Still referring to FIG. 18, ballast chamber 250 is controlled by electronic pressure controller 252, which is in turn coupled to carrier gas supply 230. The pressure of ballast chamber 250 is maintained at a predetermined pressure such that the pressure at column junction point 228 is sufficient to preferably stop the flow of the sample plug in first column 214 for a predetermined amount of time. The pressure needed to stop this flow is dependent upon the inlet pressure to the gas chromatograph.

It is important to achieve the proper pressure in ballast chamber 250 such that upon actuation of gas valve 222, a pressure pulse is applied to column junction point 228 to stop the flow in first column 214. That is, to stop the flow in first column 214 when gas valve 222 is opened, the pressure at column junction point 228 should be equal to the head pressure of carrier gas supply 224. However, it should be appreciated that due to pressure drops in the plumbing connecting ballast chamber 250 to gas valve 222 and gas valve 222 to column junction point 228 a higher pressure is required in ballast chamber 250 relative to gas chromatograph inlet pressure.

As should be appreciated from the foregoing discussion in connection with the third embodiment of the present invention, the use of a low-dead-volume valve 222 and ballast chamber 250 can be very effective in enhancing the ensemble separation of specified groups of mixture components. Furthermore, the present invention provides a simple and convenient method of controlling the selectivity in relatively small, specified regions of the ensemble chromatogram. As described in connection with the first embodiment, the third embodiment provides that all of the mixture components that are on the same column during the time that gas valve 222 is open (pulse duration) will be shifted to larger or smaller retention times, but the pattern of peaks for these components from the output second column 216 will be relatively unaffected by the pressure pulse. Lastly, gas chromatography system 210 of the present embodiment provides simpler, less expensive, more flexible method of enhancing the selectivity for series coupled, gas chromatography column ensembles, and further provides a faster pulse response than that provided by the first embodiment of the present invention.

Still further, it was seen that this method provides a number of advantages. For example, this method successfully targets individual pairs or small groups of components, and the increased resolution obtained for a targeted pair or group of components does not significantly affect the elution order or resolution of most other mixture components. Furthermore, this method eliminates the risk of inlet contamination and sample loss, which may occur if a portion of the sample is allow to vent out a vent line at the column junction point. The method described in regard to the present embodiment is particularly useful for high-speed gas chromatography with mass spectrometry detection of essential oils, such as lime oil, lemon oil, pesticides, and other environmental toxicants.

According to a fourth embodiment of the present invention, a method and apparatus are provided for achieving improved selectivity for gas chromatography with capillary columns. This fourth embodiment replaces electronic pressure controller 22 of the first embodiment with a pneumatically actuated valve connected between the column junction point and an atmospheric pressure air source. The atmospheric pressure air source could be the inlet source, which would serve to stop flow in the first column.

Figure 19:
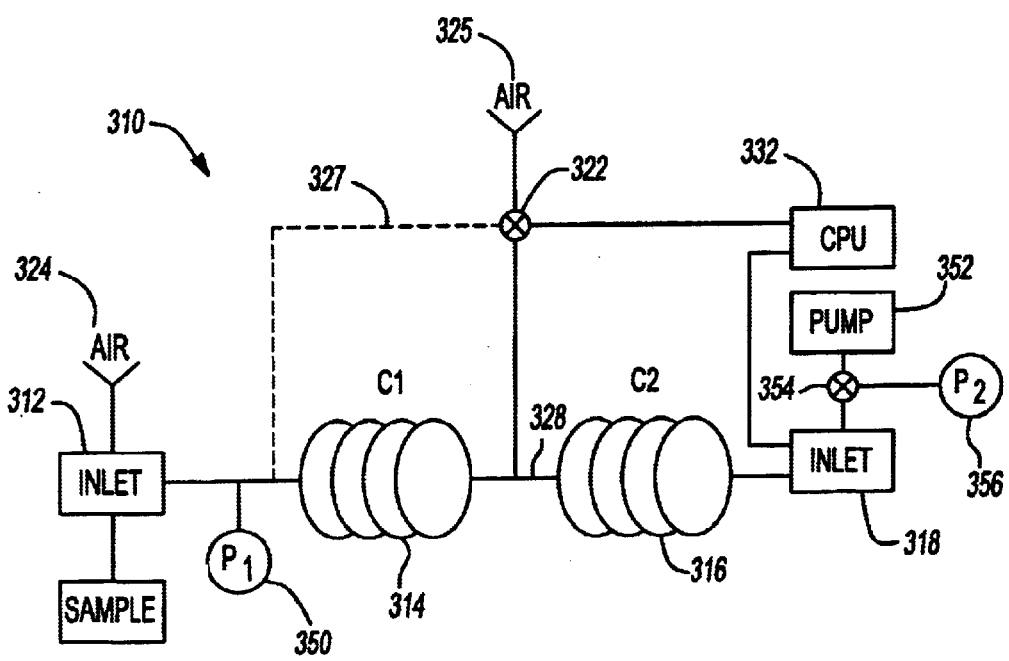
FIG. 19 is a schematic drawing illustrating a gas chromatography system according to a fourth embodiment of the present invention

According to the principles of the fourth embodiment, a low cost, low-volume gas valve 322 is coupled between a column junction point 328 and a source of atmospheric pressure air. With particular reference to FIG. 19, a dual-column, gas chromatography system is schematically illustrated in accordance with a fourth embodiment of the present invention, generally indicated at 310. Gas chromatography system 310 generally includes an inlet system 312, a first gas chromatography separation capillary column 314, a second gas chromatography capillary column 316, a detector ($D_1$) 318, and gas valve 322.

Inlet system 312 is configured generally to receive a sample "plug" of an analyte mixture for analysis within gas chromatography system 310. More particularly, a stream of carrier gas from an atmospheric pressure air supply 324 entrains such analyte mixture during injection. This entrained analyte mixture and atmospheric air composite is introduced into first column 314 through a passage 326. Various configurations of inlet system 312 can be provided, such as mechanical injection valves, cryofocusing systems, and the like.

First column 314 and second column 316 are coupled in series along column junction point 328. Gas valve 322 is fluidly coupled to column junction point 328. Gas valve 322 is preferably a pneumatically operated, low-dead-volume device, which is operated by a 50–55 psig compressed air source connected through an electronically actuated solenoid valve. Gas valve 322 is in turn coupled to an atmospheric pressure air source 325 or, alternatively, may be coupled to inlet system 312 via a line 327 (shown in phantom) to generally equalize the pressure between inlet system 312 and column junction point 328 in accordance with the principles of the present invention. Preferably, gas valve 322 is driven in response to a central processing unit 332.

Preferably, the inlet pressure of inlet system 312 is monitored by a pressure gauge 350, which is coupled to an outlet of inlet system 312. In some applications, may be necessary to provide a vacuum pump 352 located downstream of detector 318 to drive the separation. To this end, it may be necessary to include a needle valve 354 and a pressure gauge 356 positioned between detector 318 and vacuum pump 352 to facilitate the control of the pressure at the end of the column.

As discussed above in regard to the first embodiment, electronic pressure controller 22 may not afford sufficiently rapid pressure equilibration time. This can be seen in FIGS. 5a and 5b where the curves do not follow an ideal square pressure pulse. Although this may not be an issue in all applications, in those that require near ideal pressure pulses, it has been determined that the use of ballast chamber 250 is capable of providing the necessary pulse profile in many cases due to its larger volume and quicker pressure equilibration time.

Gas chromatography system 310 is much simpler than the previously recited embodiments in that only requires a single normally closed valve 322 in order to be able to stop the flow in first column 314, thereby eliminating a rather costly precision pressure controller and ballast chamber. In order to stop the flow in first column 314, the pressure at the inlet of first column 314 and column junction point 328 are equalized. This operation causes a momentary stop flow condition into first column 314, thereby further separating sample component pairs that are otherwise only barely separated at the column junction point 328.

As should be appreciated from the foregoing discussion in connection with the fourth embodiment of the present invention, the use of a low-dead-volume valve 322 and atmospheric pressure air can be very effective in enhancing the ensemble separation of specified groups of mixture components. Furthermore, the present invention provides a simple and convenient method of controlling the selectivity in relatively small, specified regions of the ensemble chromatogram. As described in connection with the first embodiment, the fourth embodiment provides that all of the mixture components that are on the same column during the time that gas valve 322 is open (pulse duration) will be shifted to larger or smaller retention times, but the pattern of peaks for these components from the output second column 316 will be relatively unaffected by the pressure pulse. Lastly, gas chromatography system 310 of the present embodiment provides simpler, less expensive, more flexible method of enhancing the selectivity for series coupled, gas chromatography column ensembles, and further provides a faster pulse response than that provided by the first embodiment of the present invention.

Still further, it was seen that this method provides a number of advantages. For example, this method successfully targets individual pairs or small groups of components, and the increased resolution obtained for a targeted pair or group of components does not significantly affect the elution order or resolution of most other mixture components.

Furthermore, this method eliminates the risk of inlet contamination and sample loss, which may occur if a portion of the sample is allowed to vent out a vent line at the column junction point.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A gas chromatography system for separating components of an analyte mixture, said gas chromatography system comprising;
   an inlet system for providing a sample of the analyte mixture entrained on a stream of atmospheric air;
   a first column fluidly coupled to said inlet system, said first column receiving said sample from said inlet system and causing at least partial separation of the components;
   a second column fluidly coupled to said first column along a column junction point, said second column receiving said components eluting from said first column, said second column causing further separation of the components;
   an ensemble detector operably coupled to said second column, said ensemble detector sensing said components eluting from said second column, said ensemble detector outputting a first signal;
   a valve member system operably coupled between said column junction point and an atmospheric pressure air source, said valve member system being selectively opened to define a fluid path between said column junction point and atmospheric pressure air source in response to a control signal to generally equalize a pressure between said column junction point and said inlet system to generally stop fluid flow through said first column for a predetermined amount of time; and
   a controller outputting said control signal.

2. The gas chromatography system according to claim 1, wherein said atmospheric pressure air source is said inlet system, whereby said valve member system is operable to fluidly couple said column junction point and said inlet system to generally equalize said pressure between said column junction point and said inlet system to generally stop fluid flow through said first column for said predetermined amount of time.

3. The gas chromatography system according to claim 1 wherein said controller comprises:
   a central processing unit operable to control said valve member system to enhance elution separation of a discrete pair of components of the analyte mixture.

4. The gas chromatography system according to claim 1 wherein said ensemble detector is a mass-spectrometer.

5. The gas chromatography system according to claim 1 wherein said ensemble detector is a surface-acoustic-wave detector.

6. The gas chromatography system according to claim 1, further comprising:
   a vacuum pump fluidly coupled downstream of said second column, said vacuum pump operable to urge said sample through said first column and said second column.

7. The gas chromatography system according to claim 6, further comprising:
   a valve operably coupled to said vacuum pump for controlling an amount of vacuum in said first column and said second column.

8. The gas chromatography system according to claim 1 wherein said valve member system comprises:
   a solenoid valve operably coupled to said controller for receiving said control signal and outputting a triggering signal;
   a low-dead-volume valve operably coupled to said solenoid valve, said low-dead-volume valve being opened in response to said triggering signal.

* * * * *